(12) United States Patent

Nie et al.

(10) Patent No.: US 12,699,101 B2

(45) Date of Patent: Aug. 4, 2026

(54) MAXIMIZING HYDROPHOBIC PEPTIDE RECOVERY USING A MASS SPECTROMETRY COMPATIBLE SURFACTANT

(71) Applicant: Regeneron Pharmaceuticals, Inc., Tarrytown, NY (US)

(72) Inventors: Song Nie, Armonk, NY (US); Reid O'Brien Johnson, Hartsdale, NY (US); Tyler Greer, Elmsford, NY (US); Xiaojing Zheng, Gaithersburg, MD (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 721 days.

(21) Appl. No.: 18/093,991

(22) Filed: Jan. 6, 2023

(65) Prior Publication Data

US 2023/0266335 A1 Aug. 24, 2023

Related U.S. Application Data

(60) Provisional application No. 63/312,225, filed on Feb. 21, 2022.

(51) Int. Cl.
*G01N 33/68* (2006.01)
*G01N 30/88* (2006.01)

(52) U.S. Cl.
CPC ......... *G01N 33/6848* (2013.01); *G01N 30/88* (2013.01); *G01N 2030/8831* (2013.01)

(58) Field of Classification Search
CPC ........... G01N 2030/8831; G01N 30/88; G01N 33/6803; G01N 33/6848
See application file for complete search history.

(56) References Cited

U.S. PATENT DOCUMENTS

| | | | | |
|---|---|---|---|---|
| 2018/0299463 A1* | 10/2018 | Piehowski | ......... | G01N 33/6848 |
| 2020/0241002 A1* | 7/2020 | Xu | ........................... | H01J 49/02 |
| 2021/0041453 A1* | 2/2021 | Benchaar | ........... | G01N 33/6848 |

FOREIGN PATENT DOCUMENTS

| | | |
|---|---|---|
| CN | 111 239 273 A | 6/2020 |

OTHER PUBLICATIONS

Tsai et al., Surfactant-assisted one-pot sample preparation for label-free single-cell proteomics, Communications Biology, 4(265): 1-12, 2021. https://doi.org/10.1038/s42003-021-01797-9.

Tsai et al., An Improved Boosting to Amplify Signal with Isobaric Labeling (iBASIL) Strategy for Precise Quantitative Single-cell Proteomics, Molecular & Cellular Proteomics 19: 828-838, May 2020. https://doi.org/10.1074/mcp.RA119.001857.

Zhang, Less is More: Membrane Protein Digestion Beyond Urea-Trypsin Solution for Next-level Proteomics, Molecular & Cellular Proteomics 14.9: 2441-2453, 2015.

(Continued)

*Primary Examiner* — Jennifer Wecker

(74) *Attorney, Agent, or Firm* — Baker Hostetler

(57) ABSTRACT

The present invention generally pertains to methods of characterizing peptides or proteins of interest. In particular, the present invention pertains to the use of the nonionic surfactant DDM to improve recovery of hydrophobic peptides in pharmacokinetic, reduced peptide mapping, or other biotherapeutic protein analyses.

18 Claims, 14 Drawing Sheets

(56)                    References Cited

OTHER PUBLICATIONS

Liu Jing et al: "High-Sensitivity N-Glycoproteomic Analysis of Mouse Brain Tissue by Protein Extraction with a Mild Detergent of N-Dodecyl [beta]-D-Maltoside", Analytical Chemistry, vol. 87, No. 4, Feb. 5, 2015 (Feb. 5, 2015), pp. 2054-2057, XP093038645, US.

Osaki Fumio et al: "Quantitative LC/ESI-SRM/MS of antibody biopharmaceuticals: use of a homologous antibody as an internal standard and three-step method development", Analytical and Bioanalytical Chemistry, Springer Berlin Heidelberg, Berlin/Heidelberg, vol. 409, No. 23, Jul. 14, 2017 (Jul. 14, 2017), pp. 5523-5532, XP036305293.

Li Hongyan et al: "General LC-MS/MS Method Approach to Quantify Therapeutic Monoclonal Antibodies Using a Common Whole Antibody Internal Standard with Application to Preclinical Studies", Analytical Chemistry, vol. 84, No. 3, Feb. 7, 2012 (Feb. 7, 2012), pp. 1267-1273.

Fresnais Margaux et al: "Development and Validation of an LC-MS-Based Quantification Assay for New Therapeutic Antibodies: Application to a Novel Therapy against Herpes Simplex Virus", ACS Omega, vol. 5, No. 38, Sep. 16, 2020 (Sep. 16, 2020), pp. 24329-24339.

Nie Song et al: "Maximizing hydrophobic peptide recovery in proteomics and antibody development using a mass spectrometry compatible surfactant", Analytical Biochemistry, Academic Press, Amsterdam, NL, vol. 658, Sep. 24, 2022 (Sep. 24, 2022).

Zhou Mowei et al: "Sensitive Top-Down Proteomics Analysis of a Low Number of Mammalian Cells Using a Nanodroplet Sample Processing Platform", Analytical Chemistry, vol. 92, No. 10, May 6, 2020 (May 6, 2020), pp. 7087-7095, XP093039143, US ISSN: 0003-2700, DOI:10.1021/acs.analchem.0c00467 Retrieved from the Internet: URL:https://pubs.acs.org/doi/pdf/10.1021/acs.analchem.0c00467?src=getftr> abstract; section "DDM was the most effective detergent among the MS-compatibledetergents tested" on pages page.

International Search Report and Written Opinion, International Application No. PCT/US2023/010294, International Filing Date Jan. 6, 2023, Date of Mailing Jun. 23, 2023.

* cited by examiner

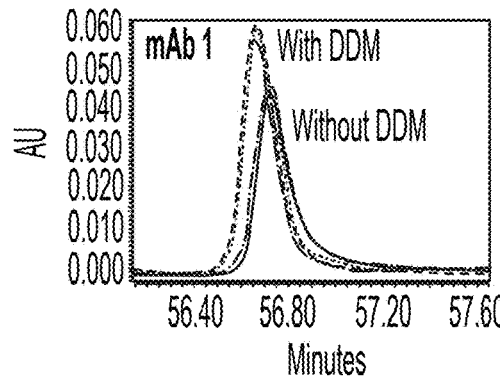
FIG. 6A
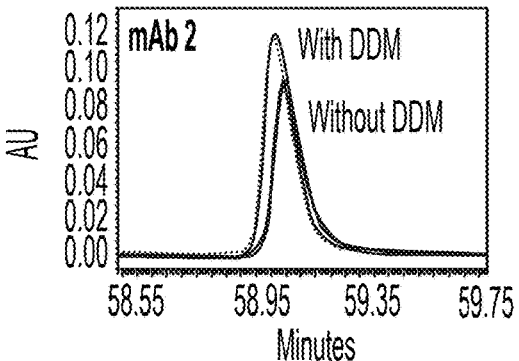
FIG. 6B
| Molecules | Assay | Peptide | Peak (min) | Average Peak Area | | | %RSD | | |
|---|---|---|---|---|---|---|---|---|---|
| | | | | Control | With DDM | Change(%) | Control | With DDM | Change(%) |
| | | HC 128-144 | 56.7 | 568303 | 675355 | +18.8% | 4.2 | 3.9 | -7.1% |
| mAb 1 | NRPM | HC 326-424 | 68.5 | 944516 | 1551617 | +64.3% | 3.7 | 1.9 | -48.6% |
| | | HC 326-431 | 69.1 | 809750 | 1223741 | +51.1% | 7.1 | 2.5 | -64.8% |
| mAb 2 | RPM | HC 101-120 | 59.1 | 711756 | 910868 | +28.0% | 2.2 | 0.6 | -72.7% |
FIG. 6C

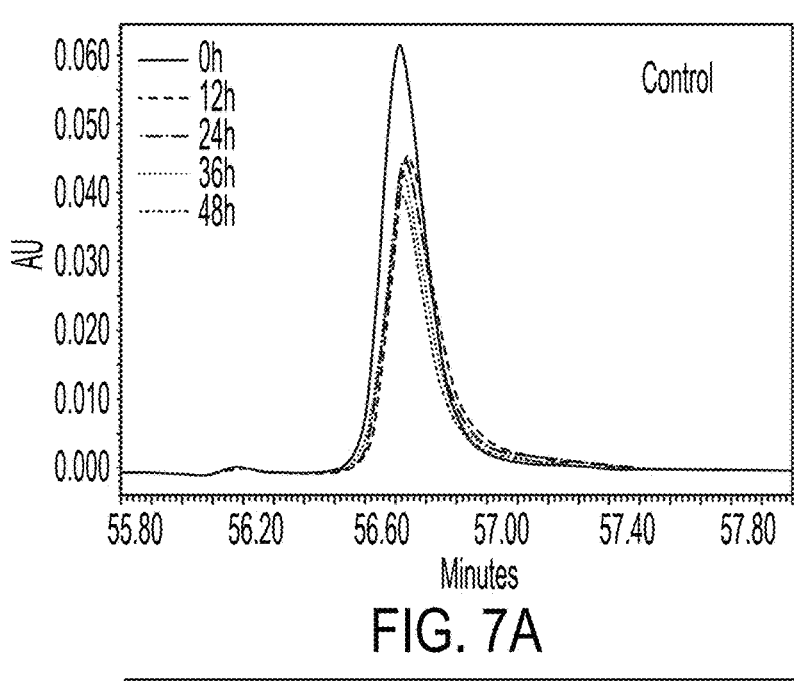
FIG. 7A
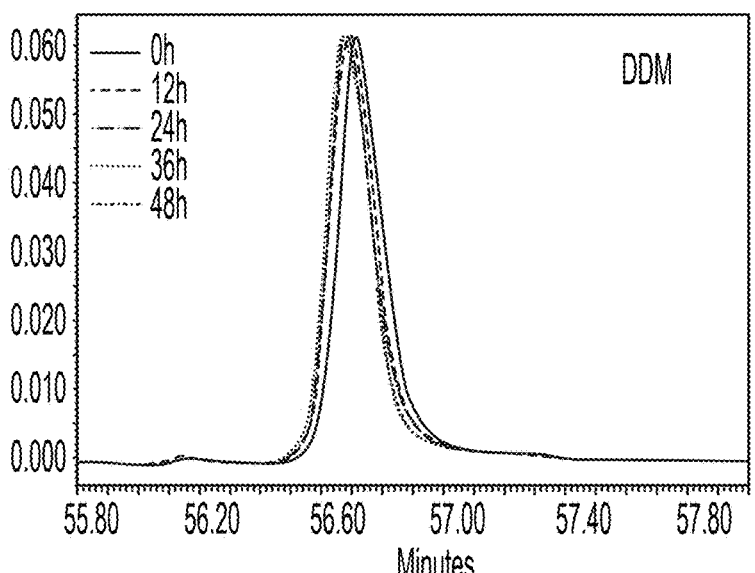
FIG. 7B
| Molecules | Assay | Peptide | Peak(min) | %RSD | | Change (%) |
|-----------|-------|---------|-----------|------|--|-----------|
| | | | | Control(48h,5 Runs) | DDM(48h,5 Runs) | |
| | | HC 128-144 | 56.7 | 6.94% | 1.48% | -78.61% |
| mAb 1 | NRPM | HC 326-424 | 68.5 | 13.81% | 4.61% | -66.62% |
| | | HC 326-431 | 69 | 21.45% | 14.39% | -32.90% |
FIG. 7C

MAXIMIZING HYDROPHOBIC PEPTIDE RECOVERY USING A MASS SPECTROMETRY COMPATIBLE SURFACTANT

CROSS-REFERENCE TO RELATED APPLICATIONS

This application claims priority to and the benefit of U.S. Provisional Patent Application No. 63/312,225, filed Feb. 21, 2022 which is herein incorporated by reference.

FIELD OF THE INVENTION

This application relates to compositions and methods for characterization of peptides and proteins.

BACKGROUND

LC-MS analysis of a protein of interest or proteomic sample can involve a number of steps, including protein extraction, concentration, fractionation, digestion, and sample dehydration. Sample loss may occur at many of the steps in a protein analysis workflow, which can impact both qualitative and quantitative results. For digested peptides, especially hydrophobic ones, nonspecific adsorption on container surfaces, such as sample tubes, autosampler vials, and pipette tips, is a common source of peptide loss.

Adsorption losses may be critical in the case of samples with limited analyte, such as single or nearly single cell samples. Peptide loss due to non-specific adsorption may also adversely affect assays involved in biotherapeutic protein drug development. For example, in pharmaceutical bioanalysis, non-specific surface adsorption of candidate peptides could cause non-linearity of calibration curves, and failure to appropriately address this issue could result in underestimating drug concentrations and lead to inaccurate pharmacokinetic assessment of an investigational drug. Additionally, when conducting peptide mapping analysis, adsorption of digested peptides to the inner surface of a container may result in failure of reproducibility and solution stability criteria during method qualification.

To minimize peptide adsorption loss, several strategies have been developed. One common strategy is to add organic solvents like dimethyl sulfoxide (DMSO) or acetonitrile (ACN) to the sample solution when a peptide sample is reconstituted or diluted, which may increase hydrophobic peptide recovery but may adversely affect hydrophilic peptide recovery. Another strategy for preventing peptide loss is to add surfactants during protein sample preparation. However, commonly used surfactants are not compatible with LC-MS analysis and must be removed before being injected into a LC-MS system, which leads to further sample loss.

Therefore, demand exists for compositions and methods for improving recovery of hydrophobic peptides in LC-MS analysis.

SUMMARY

Methods have been developed for improving recovery of hydrophobic peptides in LC-MS analysis, for example to improve detection of a peptide standard in a pharmacokinetic study, to select a suitable target peptide in a pharmacokinetic study, to improve sequence coverage in a peptide mapping analysis, or to improve sequence coverage from a dried protein sample. The methods take advantage of the properties of the nonionic surfactant DDM to prevent sample loss due to surface adsorption, particularly loss of hydrophobic peptides. For example, DDM may be added to a peptide sample to improve detection of the peptide in LC-MS analysis. DDM may also be used in a protein sample prior to enzymatic digestion to improve peptide detection in reduced or non-reduced peptide mapping. Additionally, dried peptide samples, for example samples dried by speed vacuum, may be reconstituted using DDM to improve peptide recovery prior to LC-MS analysis.

This disclosure provides a method for preparing a peptide standard for a pharmacokinetic study for liquid chromatography-mass spectrometry analysis. In some exemplary embodiments, the method comprises (a) contacting a peptide standard for a pharmacokinetic study to N-dodecyl-β-D-maltoside (DDM) to form a mixture; and (b) subjecting said mixture to liquid chromatography-mass spectrometry analysis.

In one aspect, the peptide standard comprises an amino acid sequence of a target peptide for a pharmacokinetic study. In a specific aspect, an amino acid sequence of the target peptide is selected from a complementarity-determining region of an antibody.

In one aspect, a final concentration of the peptide standard in the mixture is about 10 fmol/uL. In another aspect, a final concentration of DDM in the mixture is about 0.015%.

In one aspect, the liquid chromatography system comprises reversed-phase liquid chromatography, ion exchange chromatography, size exclusion chromatography, affinity chromatography, hydrophobic interaction chromatography, hydrophilic interaction chromatography, mixed-mode chromatography, or a combination thereof.

In one aspect, the mass spectrometer is an electrospray ionization mass spectrometer, nano-electrospray ionization mass spectrometer, or an Orbitrap-based mass spectrometer, wherein said mass spectrometer is coupled to said liquid chromatography system. In another aspect, the liquid chromatography-mass spectrometry analysis comprises parallel reaction monitoring analysis.

This disclosure also provides a method for selecting a target peptide for a pharmacokinetic study. In some exemplary embodiments, the method comprises (a) obtaining at least two candidate peptide standards comprising or having the amino acid sequence of at least two candidate target peptides for a pharmacokinetic study; (b) contacting each of said at least two candidate peptide standards to N-dodecyl-β-D-maltoside (DDM) to form at least two mixtures; (c) subjecting each of said at least two mixtures to liquid chromatography-mass spectrometry analysis to produce mass spectra for each of said at least two candidate peptide standards; (d) comparing each of said mass spectra to mass spectra produced by liquid chromatography-mass spectrometry analysis of a control mixture to produce a ratio of average peak area for each of said at least two candidate peptide standards; (e) comparing said ratio of average peak area between each of said at least two candidate peptide standards; and (f) using the comparison of (e) to select a target peptide for a pharmacokinetic study, wherein said control mixture includes the candidate peptide standard and does not include DDM.

In one aspect, an amino acid sequence of each of the at least two candidate target peptides is selected from a complementarity-determining region of an antibody. In another aspect, a final concentration of each of the at least two candidate peptide standards in each of the at least two mixtures is about 10 fmol/uL. In a further aspect, a final concentration of DDM in each of the at least two mixtures is about 0.015%.

In one aspect, the liquid chromatography system comprises reversed-phase liquid chromatography, ion exchange chromatography, size exclusion chromatography, affinity chromatography, hydrophobic interaction chromatography, hydrophilic interaction chromatography, mixed-mode chromatography, or a combination thereof.

In one aspect, the mass spectrometer is an electrospray ionization mass spectrometer, nano-electrospray ionization mass spectrometer, or an Orbitrap-based mass spectrometer, wherein said mass spectrometer is coupled to said liquid chromatography system. In another aspect, the liquid chromatography-mass spectrometry analysis comprises parallel reaction monitoring analysis.

In one aspect, the target peptide is selected on the basis of having an amino acid sequence of a candidate peptide standard having a smaller ratio of average peak area compared to the at least one other candidate peptide standard.

In one aspect, the control mixture comprises formic acid. In a specific aspect, a final concentration of formic acid in the control mixture is 0.1%.

This disclosure further provides a method for preparing a protein of interest for peptide mapping analysis. In some exemplary embodiments, the method comprises (a) subjecting a sample including a protein of interest to conditions suitable for denaturing to form a denatured sample; (b) contacting said denatured sample to at least one alkylating agent under conditions suitable for alkylation to form an alkylated sample; (c) contacting said alkylated sample to N-dodecyl-β-D-maltoside (DDM) to form a mixture; (d) contacting said mixture to at least one digestive enzyme under conditions suitable for digestion to form a peptide digest; and (e) subjecting said peptide digest to liquid chromatography-mass spectrometry for a peptide mapping analysis.

In one aspect, the peptide mapping analysis is reduced peptide mapping analysis or non-reduced peptide mapping analysis.

In one aspect, the protein of interest is an antibody, a bispecific antibody, a monoclonal antibody, a fusion protein, an antibody-drug conjugate, an antibody fragment, a host cell protein, or a protein pharmaceutical product.

In one aspect, the conditions suitable for denaturing comprise heating said sample, optionally wherein said heating is conducted at about 80° C. for about 10 minutes.

In one aspect, the method further comprises subjecting the sample to conditions suitable for reduction. In a specific aspect, the conditions suitable for reduction comprise contacting the sample to Tris (2-carboxyethyl) phosphine hydrochloride (TCEP-HCl), optionally wherein a concentration of the TCEP-HCl is about 5 mM.

In one aspect, the at least one alkylating agent comprises iodoacetamide. In another aspect, a final concentration of DDM in the mixture is about 0.1%.

In one aspect, the at least one digestive enzyme comprises trypsin, optionally wherein the trypsin is present at an enzyme to substrate ratio of about 1:10 (w/w).

In one aspect, the liquid chromatography system comprises reversed-phase liquid chromatography, ion exchange chromatography, size exclusion chromatography, affinity chromatography, hydrophobic interaction chromatography, hydrophilic interaction chromatography, mixed-mode chromatography, or a combination thereof.

In one aspect, the mass spectrometer is an electrospray ionization mass spectrometer, nano-electrospray ionization mass spectrometer, or an Orbitrap-based mass spectrometer, wherein said mass spectrometer is coupled to said liquid chromatography system. In another aspect, the liquid chromatography-mass spectrometry analysis comprises parallel reaction monitoring analysis.

This disclosure also provides a method for preparing a protein sample of interest for liquid chromatography-mass spectrometry analysis. In some exemplary embodiments, the method comprises (a) drying a protein sample of interest using a speed vacuum to form a dried sample; (b) dissolving said dried sample using a solution including N-dodecyl-β-D-maltoside (DDM) to form a reconstituted sample; and (c) subjecting said reconstituted sample to liquid chromatography-mass spectrometry analysis.

In one aspect, a concentration of DDM in the solution is about 0.015%. In another aspect, the protein sample of interest is a protein digest. In a further aspect, the protein sample of interest is a cell digest.

In one aspect, the liquid chromatography system comprises reversed-phase liquid chromatography, ion exchange chromatography, size exclusion chromatography, affinity chromatography, hydrophobic interaction chromatography, hydrophilic interaction chromatography, mixed-mode chromatography, or a combination thereof.

In one aspect, the mass spectrometer is an electrospray ionization mass spectrometer, nano-electrospray ionization mass spectrometer, or an Orbitrap-based mass spectrometer, wherein said mass spectrometer is coupled to said liquid chromatography system. In another aspect, the liquid chromatography-mass spectrometry analysis comprises parallel reaction monitoring analysis.

These, and other, aspects of the present invention will be better appreciated and understood when considered in conjunction with the following description and accompanying drawings. The following description, while indicating various embodiments and numerous specific details thereof, is given by way of illustration and not of limitation. Many substitutions, modifications, additions, or rearrangements may be made within the scope of the invention.

BRIEF DESCRIPTION OF THE DRAWINGS

FIG. 6A shows UV signals of a mAb1 peptide prepared with or without DDM, according to an exemplary embodiment.

FIG. 6B shows UV signals of a mAb2 peptide prepared with or without DDM, according to an exemplary embodiment.

FIG. 6C shows a comparison of UV signals of mAb1 and mAb2 peptides prepared with or without DDM, according to an exemplary embodiment.

FIG. 7A shows UV signals of a peptide over time in control samples, according to an exemplary embodiment.

FIG. 7B shows UV signals of a peptide over time in DDM-containing samples, according to an exemplary embodiment.

FIG. 7C shows a comparison of relative standard deviations (RSD) of UV signals of mAb1 hydrophobic peptides prepared with or without DDM after 48 hours, according to an exemplary embodiment.

DETAILED DESCRIPTION

Figure 1A:
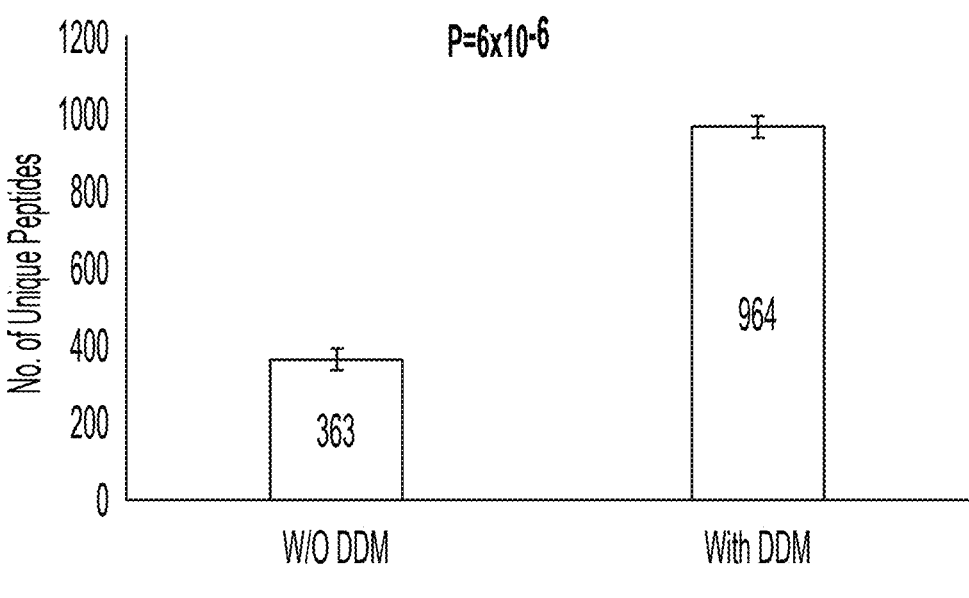
FIG. 1A shows a comparison of unique peptides identified using LC-MS/MS with and without DDM using 0.2 ng HeLa cell lysate tryptic digests (single-cell protein amount), according to an exemplary embodiment.

Proteomic sample preparation can involve a number of steps, including protein extraction, concentration, fractionation, digestion, and sample dehydration, prior to LC-MS analysis. Sample loss could occur at many of the steps in a protein analysis workflow, which can impact both qualitative and quantitative results. For digested peptides, especially hydrophobic ones, nonspecific adsorption on container surfaces, such as sample tubes, autosampler vials, and pipette tips, is a common source of peptide loss (Stejskal et al., *J Proteome Res* 2013, 12, 3057-3062; Kawashima et al., *Proteomics* 2013, 13, 751-755; Zhou et al., *Anal Chem* 2015, 87, 9802-9809; Shi et al., *Commun Biol* 2018, 1, 103; Li et al., *J Chromatogr B Analyt Technol Biomed Life Sci* 2010, 878, 583-589). With the wide application of highly sensitive LC-MS systems capable of detecting peptides at the attomole level, these adsorption losses have garnered increased attention. This is especially true in the case of samples with limited analyte such as single or nearly single cell samples, where losses through contact surface adsorption could be significant and become a critical factor for obtaining reliable data (Zhang et al., *Anal Chem* 2019, 91, 1441-1451; Tsai et al., *Commun Biol* 2021, 4, 265; Tsai et al., *Mot Cell Proteomics* 2020, 19, 828-838; Dou et al., *Anal Chem* 2019, 91, 13119-13127; Zhu et al., *Anal Chem* 2018, 90, 11756-11759; Zhu et al., *Nat Commun* 2018, 9, 882; Balasubramanian et al., *Curr Protoc* 2021, 1, e153).

Peptide loss due to non-specific adsorption is also a common issue in certain assays during biotherapeutic protein drug development (Palmgren et al., *Eur J Pharm Biopharm* 2006, 64, 369-378; Chen et al., *J Chromatogr B Analyt Technol Biomed Life Sci* 2009, 877, 943-947; Groff et al., *J Chromatogr B Analyt Technol Biomed Life Sci* 2006, 842, 122-130; Duggan, Bioanalysis 2019, 11, 797-814). For example, in pharmaceutical bioanalysis, non-specific surface adsorption of candidate peptides could cause non-linearity of calibration curves, and failure to appropriately address this issue could result in underestimating drug concentrations and lead to inaccurate pharmacokinetic assessment of an investigational drug (Li et al. 2010, Duggan).

Furthermore, peptide mapping is a key analytical method for examining the primary structure of biotherapeutic proteins (Bongers et al., *J Pharm Biomed Anal* 2000, 21, 1099-1128; Mouchahoir and Schiel, *Anal Bioanal Chem* 2018, 410, 2111-2126). However, in these analyses, some peak intensities may decrease over time due to peptide adsorption on the inner surface of sample tubes or autosampler vials, which could result in failure of reproducibility and solution stability criteria during method qualification (Bongers et al.). This adsorption can occur in a relatively short time (less than 15 minutes) based on a previous report (Mouchahoir and Schiel).

To minimize peptide adsorption loss, several strategies have been developed. One common strategy is to add organic solvents like dimethyl sulfoxide (DMSO) or acetonitrile (ACN) to the sample solution when a peptide sample is reconstituted or diluted (van Midwoud et al., *J Proteome Res* 2007, 6, 781-791). This method can increase hydrophobic peptide recovery, but it can affect the hydrophilic peptides binding to the column (van Midwoud et al.; Vatansever et al., *J Sep Sci* 2010, 33, 2478-2488). Another common strategy for preventing peptide loss is to add surfactants like sodium dodecyl sulfate (SDS) (Gan et al., *Mol Cell Proteomics* 2021, 20, 100051), CHAPS (Li et al. 2010), polysorbate 20/80 (Li et al. 2010), and PEG (Stejskal et al.; Kawashima et al.) during protein sample preparation. However, these surfactants are not compatible with LC-MS analysis and must be removed before being injected into a LC-MS system; sample losses are unavoidable during these extra detergent removal steps. At present, some commercially available LC-MS compatible surfactants like RapiGest SF (Waters), PPS Silent Surfactant and sodium deoxycholate (SDC) surfactant are used to increase protein digestion efficiency and prevent peptide loss (Scheerlinck et al., *Anal Biochem* 2015, 490, 14-19; Waas et al., *Anal Chem* 2014, 86, 1551-1559). Unfortunately, these surfactants must be removed prior to LC-MS analysis by lowering the pH of the sample, and one report found that some tryptic peptides were lost during the removal process because they co-precipitated with cleaved detergents at low pH during centrifugation and precipitation (Lin, et al., *Electrophoresis* 2010, 31, 2705-2713).

Finally, various low retention tubes or microplates have been applied to sensitive proteomics protocols in order to minimize peptide losses (Bark et al.; Weikart et al., *Future Sci OA* 2019, 5, FSO367). However, peptide loss was still observed, especially for samples containing limited analytes.

Single mammalian cells contain sub-ng levels of protein (0.1-0.5 ng) (Dou et al.; Zhu et al., *Angew Chem Int Ed Engl* 2018, 57, 12370-12374). Surface adsorption loss is a major issue for current MS-based bottom-up mammalian single cell proteomics analysis (Shi et al.; Zhang et al. 2019; Tsai et al. 2021; Zhu et al. 2018b). In recent years, significant progress has been made to improve processing recovery from low numbers of cells. One approach is to reduce sample volume to less than 200 nL, thereby reducing sample surface contact area on a special chip (nanoPOTS) (Dou et al.; Zhu et al. 2018b; Zhu et al. 2018c; Li et al., *Anal Chem* 2018, 90, 5430-5438; Cong et al., *Chem Sci* 2020, 12, 1001-1006). A second approach is to add excessive amounts of exogenous carrier protein like BSA to minimize surface adsorption of low abundance proteins and peptides in target proteomics quantitative analysis (Shi et al.; Zhang et al. 2019). A third approach is to combine a tandem mass tag (TMT) labeled sample with more than 100 cells in one channel as a carrier channel with another single cell sample channel to increase the sample starting amount (Dou et al.; Budnik et al., *Genome Biol* 2018, 19, 161). However, these approaches have disadvantages that limit their wide application. For example, special equipment is needed for nano-POTS to process samples at such a small volume, the addition of excessive exogenous carrier is only suitable for targeted proteomics analysis, and low reproducibility was reported for the TMT carrier method (Shi et al.; Zhu et al. 2018b; Budnik et al.). Recently, an easily adaptable surfactant-assisted one-pot MS (SOP-MS) method was developed to analyze single cell proteomic samples by using an MS-compatible nonionic surfactant, DDM, in low-binding PCR tubes or a microplate (Tsai et al. 2021). In this work, more than 300 proteins and about 1000 unique peptides were identified from a single mammalian cell. Other reports demonstrated that DDM can improve membrane recovery and glycoprotein identification (Liu et al., *Anal Chem* 2015, 87, 2054-2057; Zhang et al., *Mol Cell Proteomics* 2015, 14, 2441-2453). Based on these reports, DDM is potentially applicable to many different areas where prevention of sample loss is crucial because it is compatible with nanoLC-MS and relatively easy to adopt.

The disclosure herein provides a solution to reducing sample loss and improving peptide signal in biopharmaceutical analysis. In the examples set forth below, the HeLa single cell proteome was analyzed using different sample preparation methods. Significantly more proteins and unique peptides were identified in samples containing DDM compared to control samples. Further data analysis found that unique peptides identified only in DDM prepared samples have significantly higher hydrophobicity compared to the unique peptides shared in all samples.

By applying DDM to different assays in monoclonal antibody (mAb) drug development for the first time, it is demonstrated that hydrophobic CDR peptide signals could be significantly enhanced in clinical PK studies by minimizing loss from peptide adsorption. The fold change of the target peptide's intensity increase has a strong correlation with its hydrophobicity and retention time, which could provide guidance for surrogate peptide selection and peptide standard handling in clinical PK studies. In peptide mapping assays, DDM increased signal intensities of some hydrophobic peptides and improved peptide solution stability over 48 hours in an autosampler set to 4° C. In addition, it is demonstrated that improving or maximizing hydrophobic peptide recovery from samples dried in vacuo can be achieved by dissolving the dried sample in a solution containing DDM, which resulted in much higher signal for later eluting peaks and overall higher proteome coverage in complex samples.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described.

The term "a" should be understood to mean "at least one" and the terms "about" and "approximately" should be understood to permit standard variation as would be understood by those of ordinary skill in the art, and where ranges are provided, endpoints are included. As used herein, the terms "include," "includes," and "including" are meant to be non-limiting and are understood to mean "comprise," "comprises," and "comprising" respectively.

As used herein, the term "protein" or "protein of interest" can include any amino acid polymer having covalently linked amide bonds. Proteins comprise one or more amino acid polymer chains, generally known in the art as "polypeptides." "Polypeptide" refers to a polymer composed of amino acid residues, related naturally occurring structural variants, and synthetic non-naturally occurring analogs thereof linked via peptide bonds. "Synthetic peptide or polypeptide" refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may comprise one or multiple polypeptides to form a single functioning biomolecule. In another exemplary aspect, a protein can include antibody fragments, nanobodies, recombinant antibody chimeras, cytokines, chemokines, peptide hormones, and the like. Proteins of interest can include any of biotherapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. Proteins may be produced using recombinant cell-based production systems, such as the insect bacculovirus system, yeast systems (e.g., *Pichia* sp.), and mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation" (Darius Ghaderi et al., Production platforms for biotherapeutic glycoproteins. Occurrence, impact, and challenges of non-human sialylation, 28 BIOTECHNOLOGY AND GENETIC ENGINEERING REVIEWS 147-176 (2012), the entire teachings of which are herein incorporated by reference). In some exemplary embodiments, proteins comprise modifications, adducts, and other covalently linked moieties. These modifications, adducts and moieties include, for example, avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as globular proteins and fibrous proteins; conjugated proteins, such as nucleoproteins, glycoproteins, mucoproteins, chromoproteins, phosphoproteins, metalloproteins, and lipoproteins; and derived proteins, such as primary derived proteins and secondary derived proteins.

As used herein, the term "recombinant protein" refers to a protein produced as the result of the transcription and translation of a gene carried on a recombinant expression vector that has been introduced into a suitable host cell. In certain exemplary embodiments, the recombinant protein can be an antibody, for example, a chimeric, humanized, or fully human antibody. In certain exemplary embodiments, the recombinant protein can be an antibody of an isotype selected from group consisting of: IgG, IgM, IgA1, IgA2, IgD, or IgE. In certain exemplary embodiments the antibody molecule is a full-length antibody (e.g., an IgG1) or alternatively the antibody can be a fragment (e.g., an Fc fragment or a Fab fragment).

The term "antibody" as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. In different embodiments of the present invention, the FRs of the anti-big-ET-1 antibody (or antigen-binding portion thereof) may be identical to the human germline sequences or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, for example, from full antibody molecules using any suitable standard techniques such as proteolytic digestion or recombinant genetic engineering techniques involving the manipulation and expression of DNA encoding antibody variable and optionally constant domains. Such DNA is known and/or is readily available from, for example, commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. In some exemplary embodiments, an antibody fragment comprises a sufficient amino acid sequence of the parent antibody of which it is a fragment that it binds to the same antigen as does the parent antibody; in some exemplary embodiments, a fragment binds to the antigen with a comparable affinity to that of the parent antibody and/or competes with the parent antibody for binding to the antigen. An antibody fragment may be produced by any means. For example, an antibody fragment may be enzymatically or chemically produced by fragmentation of an intact antibody and/or it may be recombinantly produced from a gene encoding the partial antibody sequence. Alternatively, or additionally, an antibody fragment may be wholly or partially synthetically produced. An antibody fragment may optionally comprise a single chain antibody fragment. Alternatively, or additionally, an antibody fragment may comprise multiple chains that are linked together, for example, by disulfide linkages. An antibody fragment may optionally comprise a multi-molecular complex. A functional antibody fragment typically comprises at least about 50 amino acids and more typically comprises at least about 200 amino acids.

The term "bispecific antibody" includes an antibody capable of selectively binding two or more epitopes. Bispecific antibodies generally comprise two different heavy chains with each heavy chain specifically binding a different epitope—either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions and such sequences can be expressed in a cell that expresses an immunoglobulin light chain. A typical bispecific antibody has two heavy chains each having three heavy chain CDRs, followed by a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding of one or both of the heavy chains to one or both epitopes. BsAbs can be divided into two major classes, those bearing an Fc region (IgG-like) and those lacking an Fc region, the latter normally being smaller than the IgG and IgG-like bispecific molecules comprising an Fc. The IgG-like bsAbs can have different formats such as, but not limited to, triomab, knobs into holes IgG (kih IgG), crossMab, orth-Fab IgG, Dual-variable domains Ig (DVD-Ig), two-in-one or dual action Fab (DAF), IgG-single-chain Fv (IgG-scFv), or κλ-bodies. The non-IgG-like different formats include tandem scFvs, diabody format, single-chain diabody, tandem diabodies (TandAbs), Dual-affinity retargeting molecule (DART), DART-Fc, nanobodies, or antibodies produced by the dock-and-lock (DNL) method (Gaowei Fan, Zujian Wang & Mingju Hao, Bispecific antibodies and their applications, 8 JOURNAL OF HEMATOLOGY & ONCOLOGY 130; Dafne Muller & Roland E. Kontermann, Bispecific Antibodies, HAND-BOOK OF THERAPEUTIC ANTIBODIES 265-310 (2014), the entire teachings of which are herein incorporated). The methods of producing bsAbs are not limited to quadroma technology based on the somatic fusion of two different hybridoma cell lines, chemical conjugation, which involves chemical cross-linkers, and genetic approaches utilizing recombinant DNA technology.

As used herein "multispecific antibody" refers to an antibody with binding specificities for at least two different antigens. While such molecules normally will only bind two antigens (i.e., bispecific antibodies, bsAbs), antibodies with additional specificities such as trispecific antibody and KIH Trispecific can also be addressed by the system and method disclosed herein.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

As used herein, a "sample" can be obtained from any step of a bioprocess, such as cell culture fluid (CCF), harvested cell culture fluid (HCCF), any step in the downstream processing, drug substance (DS), or a drug product (DP) comprising the final formulated product. In some specific exemplary embodiments, the sample can be selected from any step of the downstream process of clarification, chromatographic production, or filtration.

In some exemplary embodiments, a sample including a protein of interest can be prepared prior to LC-MS analysis. Preparation steps can include denaturation, alkylation, dilution, and digestion.

As used herein, the term "protein alkylating agent" or "alkylation agent" refers to an agent used for alkylating certain free amino acid residues in a protein. Non-limiting examples of protein alkylating agents are iodoacetamide (IOA/IAA), chloroacetamide (CAA), acrylamide (AA), N-ethylmaleimide (NEM), methyl methanethiosulfonate (MMTS), and 4-vinylpyridine or combinations thereof.

As used herein, "protein denaturing" or "denaturation" can refer to a process in which the three-dimensional shape of a molecule is changed from its native state. Protein denaturation can be carried out using a protein denaturing agent. Non-limiting examples of a protein denaturing agent include heat, high or low pH, reducing agents like DTT, or exposure to chaotropic agents. Several chaotropic agents can be used as protein denaturing agents. Chaotropic solutes increase the entropy of the system by interfering with intramolecular interactions mediated by non-covalent forces such as hydrogen bonds, van der Waals forces, and hydrophobic effects. Non-limiting examples of chaotropic agents include butanol, ethanol, guanidinium chloride, lithium perchlorate, lithium acetate, magnesium chloride, phenol, propanol, sodium dodecyl sulfate, thiourea, N-lauroylsarcosine, urea, and salts thereof.

As used herein, the term "digestion" refers to hydrolysis of one or more peptide bonds of a protein. There are several approaches to carrying out digestion of a protein in a sample using an appropriate hydrolyzing agent, for example, enzymatic digestion or non-enzymatic digestion. Digestion of a protein into constituent peptides can produce a "peptide digest" that can further be analyzed using peptide mapping analysis.

As used herein, the term "digestive enzyme" refers to any of a large number of different agents that can perform digestion of a protein. Non-limiting examples of hydrolyzing agents that can carry out enzymatic digestion include protease from *Aspergillus Saitoi*, elastase, subtilisin, protease XIII, pepsin, trypsin, Tryp-N, chymotrypsin, aspergillopepsin I, Lys-N protease (Lys-N), Lys-C endoproteinase (Lys-C), endoproteinase Asp-N (Asp-N), endoproteinase Arg-C (Arg-C), endoproteinase Glu-C (Glu-C) or outer membrane protein T (OmpT), immunoglobulin-degrading enzyme of *Streptococcus pyogenes* (IdeS), thermolysin, papain, pronase, V8 protease or biologically active fragments or homologs thereof or combinations thereof. For a recent review discussing the available techniques for protein digestion see Switazar et al., "Protein Digestion: An Overview of the Available Techniques and Recent Developments" (Linda Switzar, Martin Giera & Wilfried M. A. Niessen, Protein Digestion: An Overview of the Available Techniques and Recent Developments, 12 JOURNAL OF PROTEOME RESEARCH 1067-1077 (2013)).

As used herein, the term "protein reducing agent" or "reduction agent" refers to the agent used for reduction of disulfide bridges in a protein. Non-limiting examples of protein reducing agents used to reduce a protein are dithiothreitol (DTT), β-mercaptoethanol, Ellman's reagent, hydroxylamine hydrochloride, sodium cyanoborohydride, tris(2-carboxyethyl)phosphine hydrochloride (TCEP-HCl), or combinations thereof. A conventional method of protein analysis, reduced peptide mapping, involves protein reduction prior to LC-MS analysis. In contrast, non-reduced peptide mapping omits the sample preparation step of reduction in order to preserve endogenous disulfide bonds.

As used herein, the term "pharmacokinetics" (PK) refers to a field of study dealing with features of a drug after administration to a subject. Exemplary components of pharmacokinetic analysis include liberation of a drug from a pharmaceutical formulation, absorption of a drug into blood circulation, distribution of a drug throughout the body, metabolism (also called biotransformation) of a drug into metabolites, and excretion of a drug from a body. Pharmacokinetics of a drug are a key feature for evaluation of a biotherapeutic candidate. In particular, a pharmacokinetic study may be conducted to evaluate how levels of a drug and its modified forms and metabolites change over time after administration to a subject. Biotherapeutic proteins may be evaluated through the analysis of representative peptides, or "target peptides" or "surrogate peptides," using liquid chromatography-mass spectrometry. A peptide may be a suitable target peptide if it is unique to or strongly representative of a protein, for example a complementarity-determining region of an antibody, and if it can be reliably recovered and measured.

The examples set forth in this disclosure show that the suitability of candidate target peptides may be dependent on their hydrophobicity, with more hydrophobic peptides being more vulnerable to sample loss due to surface adsorption. Using the method of the present invention, it is possible to evaluate candidate target peptides for their vulnerability to sample loss by comparing the recovery of synthetic peptide standards having the same amino acid sequence as candidate target peptides prepared with or without DDM, using LC-MS analysis. A peptide that has a large ratio of average peak area between DDM-containing and control samples may be more vulnerable to sample loss due to surface adsorption and may therefore be considered less suitable for selection as a target peptide.

Synthetic peptide standards are useful in pharmacokinetic studies in order to generate a standard curve, which determines a mathematical relationship between LC-MS signal and peptide concentration that can then be used to calculate the concentration of a target peptide. Measurement of peptide standards, and therefore overall pharmacokinetic analysis, may be adversely impacted by surface adsorption of a peptide standard to a container. The method of the present invention can be used to improve retention of peptide standards for pharmacokinetic studies, by using DDM when preparing peptide standards to prevent surface adsorption and sample loss.

As used herein, the term "liquid chromatography" refers to a process in which a biological/chemical mixture carried by a liquid can be separated into components as a result of differential distribution of the components as they flow through (or into) a stationary liquid or solid phase. Non-limiting examples of liquid chromatography include reversed-phase liquid chromatography, ion-exchange chromatography, size exclusion chromatography, affinity chromatography, hydrophobic interaction chromatography, hydrophilic interaction chromatography, or mixed-mode chromatography. In some aspects, the sample containing the at least one protein of interest or peptide digest can be subjected to any one of the aforementioned chromatographic methods or a combination thereof. Analytes separated using chromatography will feature distinctive retention times, reflecting the speed at which an analyte moves through the chromatographic column. Analytes may be compared using a chromatogram, which plots retention time on one axis and measured signal on another axis, where the measured signal may be produced from, for example, UV detection or fluorescence detection.

As used herein, the term "mass spectrometer" includes a device capable of identifying specific molecular species and measuring their accurate masses. The term is meant to include any molecular detector into which a polypeptide or peptide may be characterized. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization) or through separate processes. The choice of ion source depends on the application.

In some exemplary embodiments, the mass spectrometer can be a tandem mass spectrometer. As used herein, the term "tandem mass spectrometry" includes a technique where structural information on sample molecules is obtained by using multiple stages of mass selection and mass separation. A prerequisite is that the sample molecules be transformed into a gas phase and ionized so that fragments are formed in a predictable and controllable fashion after the first mass selection step. MS/MS, or $MS^2$, can be performed by first selecting and isolating a precursor ion ($MS^1$), and fragmenting it to obtain meaningful information. Tandem MS has been successfully performed with a wide variety of analyzer combinations. Which analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time, mass spectrometer ions produced in the ion source can be trapped, isolated, fragmented, and m/z separated in the same physical device.

The peptides identified by the mass spectrometer can be used as surrogate representatives of the intact protein, their abundance, their post-translational modifications or other modifications. They can be used for protein characterization by correlating experimental and theoretical MS/MS data, the latter generated from possible peptides in a protein sequence database. The characterization includes, but is not limited to, sequencing amino acids of the protein fragments, determining protein sequencing, determining protein de novo sequencing, locating post-translational modifications or sequence variants, or identifying post-translational modifications or sequence variants, or comparability analysis, or combinations thereof.

In some exemplary aspects, the mass spectrometer can work on nanoelectrospray or nanospray. The term "nanoelectrospray" or "nanospray" as used herein refers to electrospray ionization at a very low solvent flow rate, typically hundreds of nanoliters per minute of sample solution or lower, often without the use of an external solvent delivery. The electrospray infusion setup forming a nanoelectrospray can use a static nanoelectrospray emitter or a dynamic nanoelectrospray emitter. A static nanoelectrospray emitter performs a continuous analysis of small sample (analyte) solution volumes over an extended period of time. A dynamic nanoelectrospray emitter uses a capillary column and a solvent delivery system to perform chromatographic separations on mixtures prior to analysis by the mass spectrometer.

In some exemplary embodiments, mass spectrometry can be performed under native conditions. As used herein, the term "native conditions" can include performing mass spectrometry under conditions that preserve non-covalent interactions in an analyte. For a detailed review on native MS, refer to the review: Elisabetta Boeri Erba & Carlo Petosa, The emerging role of native mass spectrometry in characterizing the structure and dynamics of macromolecular complexes, 24 PROTEIN SCIENCE 1176-1192 (2015).

As used herein, the term "database" refers to a compiled collection of protein sequences that may possibly exist in a sample, for example in the form of a file in a FASTA format. Relevant protein sequences may be derived from cDNA sequences of a species being studied. Public databases that may be used to search for relevant protein sequences included databases hosted by, for example, Uniprot or Swiss-prot. Databases may be searched using what are herein referred to as "bioinformatics tools." Bioinformatics tools provide the capacity to search uninterpreted MS/MS spectra against all possible sequences in the database(s), and provide interpreted (annotated) MS/MS spectra as an output. Non-limiting examples of such tools are Mascot (www.matrixscience.com), Spectrum Mill (www.chem.agilent.com), PLGS (www.waters.com), PEAKS (www.bioinformaticssolutions.com), Proteinpilot (download.appliedbiosystems-.com/proteinpilot), Phenyx (www.phenyx-ms.com), Sorcerer (www.sagenresearch.com), OMS SA (www.pubchem.ncbi.nlm.nih.gov/omssa/), X!Tandem (www.thegpm.org/TANDEM/), Protein Prospector (prospector.ucsfedu/prospector/mshome.htm), Byonic (www.proteinmetrics.com/products/byonic) or Sequest (fields.scripps.edu/sequest).

This disclosure provides a method for preparing a peptide standard for a pharmacokinetic study for liquid chromatography-mass spectrometry analysis. In some exemplary embodiments, the method comprises (a) contacting a peptide standard for a pharmacokinetic study to N-dodecyl-β-D-maltoside (DDM) to form a mixture; and (b) subjecting said mixture to liquid chromatography-mass spectrometry analysis.

In some exemplary embodiments, the peptide standard comprises or has an amino acid sequence of a target peptide for a pharmacokinetic study. In further exemplary embodiments, an amino acid sequence of the target peptide may be selected from a complementarity-determining region of an antigen-binding protein. An antigen-binding protein may be selected from, for example, a monoclonal antibody, a bispecific antibody, a multispecific antibody, or a fusion protein.

In some exemplary embodiments, a final concentration of the peptide standard in the mixture may be between about 0.1 fmol/μL and about 100 fmol/μL, between about 1 fmol/μL and about 20 fmol/μL, between about 5 fmol/μL and about 15 fmol/μL, about 1 fmol/μL, about 2 fmol/μL, about 3 fmol/μL, about 4 fmol/μL, about 5 fmol/μL, about 6 fmol/μL, about 7 fmol/μL, about 8 fmol/μL, about 9 fmol/μL, about 10 fmol/μL, about 11 fmol/μL, about 12 fmol/μL, about 13 fmol/μL, about 14 fmol/μL, about 15 fmol/μL, about 16 fmol/μL, about 17 fmol/μL, about 18 fmol/μL, about 19 fmol/μL, about 20 fmol/μL, about 30 fmol/μL, about 40 fmol/μL, about 50 fmol/μL, or about 100 fmol/μL.

In some exemplary embodiments, a final concentration of DDM in the mixture may be between about 0.001% and about 0.05%, between about 0.01% and about 0.02%, about 0.001%, about 0.002%, about 0.003%, about 0.004%, about 0.005%, about 0.006%, about 0.007%, about 0.008%, about 0.009%, about 0.01%, about 0.011%, about 0.012%, about 0.013%, about 0.014%, about 0.015%, about 0.016%, about 0.017%, about 0.018%, about 0.019%, about 0.02%, about 0.03%, about 0.04%, about 0.05%, or about 0.1%.

This disclosure also provides a method for selecting a target peptide for a pharmacokinetic study. In some exemplary embodiments, the method comprises (a) obtaining at least two candidate peptide standards comprising or having the amino acid sequence of at least two candidate target peptides for a pharmacokinetic study; (b) contacting each of said at least two candidate peptide standards to N-dodecyl-β-D-maltoside (DDM) to form at least two mixtures; (c) subjecting each of said at least two mixtures to liquid chromatography-mass spectrometry analysis to produce mass spectra for each of said at least two candidate peptide standards; (d) comparing each of said mass spectra to mass spectra produced by liquid chromatography-mass spectrometry analysis of a control mixture to produce a ratio of average peak area for each of said at least two candidate peptide standards; (e) comparing said ratio of average peak area between each of said at least two candidate peptide standards; and (f) using the comparison of (e) to select a target peptide for a pharmacokinetic study, wherein said control mixture includes the candidate peptide standard and does not include DDM.

In some exemplary embodiments, an amino acid sequence of each of the at least two candidate target peptides may be selected from a complementarity-determining region of an antigen-binding protein.

In some exemplary embodiments, a final concentration of each of the at least two candidate peptide standards in each of the at least two mixtures may be between about 0.1 fmol/μL and about 100 fmol/μL, between about 1 fmol/μL and about 20 fmol/μL, between about 5 fmol/μL and about 15 fmol/μL, about 1 fmol/μL, about 2 fmol/μL, about 3 fmol/μL, about 4 fmol/μL, about 5 fmol/μL, about 6 fmol/μL, about 7 fmol/μL, about 8 fmol/μL, about 9 fmol/μL, about 10 fmol/μL, about 11 fmol/μL, about 12 fmol/μL, about 13 fmol/μL, about 14 fmol/μL, about 15 fmol/μL, about 16 fmol/μL, about 17 fmol/μL, about 18 fmol/μL, about 19 fmol/μL, about 20 fmol/μL, about 30 fmol/μL, about 40 fmol/μL, about 50 fmol/μL, or about 100 fmol/μL.

In some exemplary embodiments, a final concentration of DDM in each of the at least two mixtures may be between about 0.001% and about 0.05%, between about 0.01% and about 0.02%, about 0.001%, about 0.002%, about 0.003%, about 0.004%, about 0.005%, about 0.006%, about 0.007%, about 0.008%, about 0.009%, about 0.01%, about 0.011%, about 0.012%, about 0.013%, about 0.014%, about 0.015%, about 0.016%, about 0.017%, about 0.018%, about 0.019%, about 0.02%, about 0.03%, about 0.04%, about 0.05%, or about 0.1%.

In some exemplary embodiments, the control mixture may comprise formic acid. Formic acid may be present in the control mixture at a concentration of between about 0.01% and about 0.5%, between about 0.05% and about 0.2%, about 0.01%, about 0.02%, about 0.03%, about 0.04%, about 0.05%, about 0.06%, about 0.07%, about 0.08%, about 0.09%, about 0.1%, about 0.11%, about 0.12%, about 0.13%, about 0.14%, about 0.15%, about 0.2%, about 0.3%, about 0.4%, or about 0.5%.

This disclosure further provides a method for preparing a protein of interest for peptide mapping analysis. In some exemplary embodiments, the method comprises (a) subjecting a sample including a protein of interest to conditions suitable for denaturing to form a denatured sample; (b) contacting said denatured sample to at least one alkylating agent under conditions suitable for alkylation to form an alkylated sample; (c) contacting said alkylated sample to N-dodecyl-β-D-maltoside (DDM) to form a mixture; (d) contacting said mixture to at least one digestive enzyme under conditions suitable for digestion to form a peptide digest; and (e) subjecting said peptide digest to liquid chromatography-mass spectrometry for a peptide mapping analysis.

In some exemplary embodiments, the conditions suitable for denaturing may comprise heating the sample. The sample may be heated at between about 40° C. and about 100° C., about 45° C., about 50° C., about 55° C., about 60° C., about 65° C., about 70° C., about 75° C., about 80° C., about 85° C., about 90° C., about 95° C., or about 100° C. The sample may be heated for between about 5 minutes and about 20 minutes, about 5 minutes, about 10 minutes, about 15 minutes, or about 20 minutes.

In some exemplary embodiments, the method further comprises subjecting the sample to conditions suitable for reduction. In some exemplary embodiments, conditions suitable for reduction may comprise contacting the sample to Tris (2-carboxyethyl) phosphine hydrochloride (TCEP-HCl), wherein a concentration of the TCEP-HCl may be between about 1 mM and about 20 mM, about 1 mM, about 2 mM, about 3 mM, about 4 mM, about 5 mM, about 6 mM, about 7 mM, about 8 mM, about 9 mM, about 10 mM, about 15 mM, or about 20 mM.

In some exemplary embodiments, a final concentration of DDM in the mixture may be between about 0.01% and about 0.5%, between about 0.05% and about 0.2%, about 0.01%, about 0.02%, about 0.03%, about 0.04%, about 0.05%, about 0.06%, about 0.07%, about 0.08%, about 0.09%, about 0.1%, about 0.11%, about 0.12%, about 0.13%, about 0.14%, about 0.15%, about 0.2%, about 0.3%, about 0.4%, or about 0.5%.

This disclosure also provides a method for preparing a protein sample of interest for liquid chromatography-mass spectrometry analysis. In some exemplary embodiments, the method comprises (a) drying a protein sample of interest using a speed vacuum to form a dried sample; (b) dissolving said dried sample using a solution including N-dodecyl-β-D-maltoside (DDM) to form a reconstituted sample; and (c) subjecting said reconstituted sample to liquid chromatography-mass spectrometry analysis.

In some exemplary embodiments, a concentration of DDM in the solution may be between about 0.001% and about 0.05%, between about 0.01% and about 0.02%, about 0.001%, about 0.002%, about 0.003%, about 0.004%, about 0.005%, about 0.006%, about 0.007%, about 0.008%, about 0.009%, about 0.01%, about 0.011%, about 0.012%, about 0.013%, about 0.014%, about 0.015%, about 0.016%, about 0.017%, about 0.018%, about 0.019%, about 0.02%, about 0.03%, about 0.04%, about 0.05%, or about 0.1%.

It is understood that the present invention is not limited to any of the aforesaid peptide(s), protein(s), protein(s) of interest, antibody(s), protein alkylating agent(s), protein denaturing agent(s), protein reducing agent(s), digestive enzyme(s), sample(s), chromatographic method(s), mass spectrometer(s), database(s), bioinformatics tool(s), pH, temperature(s), or concentration(s), and any peptide(s), protein(s), protein(s) of interest, antibody(s), protein alkylating agent(s), protein denaturing agent(s), protein reducing agent(s), digestive enzyme(s), sample(s), chromatographic method(s), mass spectrometer(s), database(s), bioinformatics tool(s), pH, temperature(s), or concentration(s) can be selected by any suitable means.

The present invention will be more fully understood by reference to the following examples. They should not, however, be construed as limiting the scope of the invention.

EXAMPLES

Materials and Methods

1. Chemicals and Reagents

Formic acid (FA), trifluoroacetic acid (TFA), and LC-MS grade acetonitrile were purchased from Thermo Fisher Scientific (Rockford, IL). N-dodecyl-β-D-maltoside (DDM), iodoacetamide (IAM) and Dithiothreitol (DTT) were purchased from Sigma-Aldrich (St. Louis, MO). Sequencing grade modified trypsin with resuspension buffer was procured from Promega (Madison, WI) and ultrapure 1 M Tris-HCl buffer (pH 7.5) was obtained from Invitrogen (Carlsbad, CA). Purified monoclonal antibody (mAb) drug substances were produced internally by Regeneron (Tarrytown, NY). AQUA' grade custom synthetic standard mAb peptides, HeLa cell lysate protein digests and BSA digests were ordered from Thermo Fisher Scientific (Rockford, IL). NANOSEP 30K OMEGA centrifugal filters were acquired from Pall Life Sciences (Port Washington, NY). Protein LoBind tubes were purchased from Eppendorf (Enfield, CT), and glass insert sample vials were obtained from Waters (Milford, MA).

2. Sample Preparation

HeLa cell lysate protein digests were diluted to 0.05 ng/μL by 0.1% FA or 0.015% DDM solution, and 0.2 ng (4 μL) was injected onto the LC-MS to simulate single cell sample analysis. Sixteen synthetic peptides from a mAb's constant region and CDR were diluted and mixed to a final concentration of 10 fmol/μL by 0.1% FA, 0.015% DDM solution or complex cell digest matrix. In reconstitution experiments, 20 μL of 500 fmol/μL BSA digests and 200 ng/μL HeLa digests were aliquoted into vials and dried in vacuo. Dried samples were reconstituted by 0.1% FA or 0.015% DDM solution. One picomole BSA digests and 100 ng HeLa digests were loaded onto the column for nanoLC-MS/MS analysis.

3. Peptide Mapping Sample Preparation of mAb

A 550 μg aliquot of each mAb sample diluted to about 10 μg/μL by $H_2O$ was centrifuged by a NANOSEP 30K filter. After reconstitution in 5 mM acetic acid, protein concentration was measured using a NanoDrop 2000 (Thermo Scientific, MA) UV-Vis spectrophotometer. For reduced peptide mapping (RPM) samples, a 100 μg aliquot of each sample was denatured and reduced in 42 μL of solution containing 5 mM acetic acid and 5 mM Tris (2-carboxyethyl) phosphine hydrochloride (TCEP-HCl) by heating at 80° C. for 10 minutes. Subsequently, 24 μL of 8 M urea and 2 μL of 0.2 M iodoacetamide was added to each sample for alkylation and incubated for 30 minutes in the dark. Each sample was then diluted with 100 mM Tris-HCl, pH 7.5 and DDM solution to a final concentration of 0.1% DDM and digested with trypsin at an enzyme to substrate ratio of 1:10 (w/w) at 37° C. for 3 hours. The digestion was quenched by adding TFA to a final concentration of 0.3%. For non-reduced peptide mapping (NRPM) samples, a 100 μg aliquot of each sample was denatured by heating at 80° C. for 10 min. After cooling down to room temperature, the denatured samples were alkylated by adding 2 μL of 0.2 M iodoacetamide and incubated at room temperature in the dark for 30 minutes. All subsequent steps are identical to the reduced peptide mapping sample preparation.

4. NanoLC-MS Analysis

Single cell samples and reconstituted samples were analyzed using an UltiMate 3000 RSLCnano system (Thermo Scientific) coupled to an Orbitrap Exploris 480 mass spectrometer (Thermo Scientific). A 30 μm ID×25 cm C18 column was used for single cell sample analysis, and a 75 μm ID×25 cm C18 column was used for all other sample analysis (CoAnn Technologies, 360 μm OD). Mobile phase A contained 0.1% FA in water and mobile phase B contained 0.1% FA in 80% acetonitrile/20% water. All samples were loaded on an Acclaim PepMap 100, 75 μm×2 cm pre-column (Thermo Scientific) for 5 minutes at a flow rate of 5 μL/min. For single cell samples, a linear LC gradient with 60 nL/min flow rate was set up as follows: 5% B at 0 min, 8% B at 5 min, 40% B at 80 min, and 95% B from 95-120 min. For other samples, a 0.25 μl/min flow rate was used, and the LC gradient was as follows: 5% B at 0 min, 8% B at 3 min, 36% B at 95 min, and 95% B from 120-130 min.

Mass spectra data acquisition was performed using Xcalibur v4.3 (Thermo Fisher Scientific, CA). For single cell sample analysis, the nano ESI spray voltage was set at 2100 V. In traditional data dependent acquisition mode (DDA), top 10 peaks were selected for MS/MS fragmentation. MS full scans were acquired from m/z 375-1575 at 120K resolution (m/z 200) with 400% standard automated gain control (AGC), and a maximum injection time of 100 ms. MS/MS fragmentation was performed using HCD with a normalized collision energy of 30% at a resolution of 30K (m/z 200), 100% standard AGC, and a maximum injection time of 500 ms. Dynamic exclusion duration was set to 60 seconds with a single repeat count, and only precursors with charge states of +2 to +7 were selected.

For other sample analyses, a 2200 V spray voltage was used, and a survey scan was performed in the Orbitrap with a cycle time of 1.5 seconds. MS full scans were acquired from m/z 400-1800 at 60K resolution (m/z 200) with 300% standard automated gain control (AGC), and a maximum injection time of 20 ms. MS/MS fragmentation was performed using HCD with a normalized collision energy of 30% at a resolution of 15K (m/z 200) and a maximum injection time of 50 ms. All other MS parameters are identical to the single cell sample analysis.

5. Target Quantification by Parallel Reaction Monitoring (PRM)

PRM target quantification was performed on an Orbitrap Exploris 480 mass spectrometer equipped with an UltiMate 3000 RSLCnano system and 75 μm ID×25 cm C18 column (CoAnn Technologies, 360 μm OD). A short gradient with a flow rate of 0.3 μL/min was set up as follows: 5% B at 0 min, 8% B at 3 min, 40% B at 20 min, and 95% B from 30-35 min. The m/z of the most intense surrogate peptide peak was selected for PRM analysis with 5 minutes windows. MS/MS spectra were acquired using HCD with a normalized collision energy of 30% at a resolution of 30K (m/z 200) and a maximum injection time of 100 ms.

6. UPLC/UV-MS Analysis

A Waters ACQUITY UPLC I-Class system coupled to a Thermo Scientific Q Exactive Plus mass spectrometer was used to analyze the peptide mapping samples. The tryptic peptide mixture was separated by a Waters ACQUITY UPLC BEH® 130 C18 column (1.7 μm, 2.1 mm×150 mm) at a flow rate of 0.25 mL/minute. Mobile phase A (MPA) was 0.05% TFA in water, and mobile phase B (MPB) was 0.045% TFA in acetonitrile. The gradient was held at 0.1% B for the first 5 min and then increased to 35% B in 75 min followed by another increase to 90% B in 5 min. The column was equilibrated with 99.9% mobile phase A prior to sample injection, with the column temperature maintained at 40° C. The MS data were acquired on a Thermo Scientific Q Exactive Plus mass spectrometer from m/z 300-2000 at a resolution of 70K (at m/z 400), followed by five data-dependent MS/MS scans at a resolution of 17.5K. MS full scans were set at $1\times10^6$ automated gain control (AGC) and a maximum injection time of 50 ms. MS/MS fragmentation was performed using higher-energy C-trap dissociation (HCD) with a normalized collision energy of 28% at a $1\times10^5$ AGC and a maximum injection time of 100 ms. Dynamic exclusion duration was set to 15 s with a single repeat count.

7. Data Analysis

Database searches for protein identification were performed using SEQUEST and Mascot embedded into Proteome Discoverer 2.2 (Thermo Fisher Scientific). The human UniProt target-decoy protein database including common contaminants was used for HeLa sample database searches. Precursor ion mass tolerance was set to 20 ppm and fragment ion mass tolerance was set to 0.02 Da. Trypsin was specified as the digestion enzyme during the database search with one missed cleavage allowed. Methionine oxidation (+16 Da) was selected as a variable modification and cysteine carbamidomethylation was chosen as a fixed modification for the normal (alkylated) digests. False discovery rates (FDRs) were set to 1% for peptide identification and 5% for protein identification. Peptide mapping and BSA sample data were analyzed using Protein Metrics Byonic™ (version 3.11.3) by searching the raw files against the mAb or BSA protein sequence. All peptide quantification was executed using Skyline Daily software (University of Washington, WA) by extracting the MS' peak area of all detected charge states. The three most intense fragment peaks free of interference were selected for PRM target quantification. Empower (Milford, MA) was employed to extract UV chromatogram peak areas. The peptide hydrophobicity was calculated using the Peptide Synthesis and Proteotypic Peptide Analyzing Tool from ThermoFisher Scientific (Waltham, MA). GraphPad Prism 9.0.2 (San Diego, CA) was used for correlation analysis and p-value calculation.

Figure 1B:
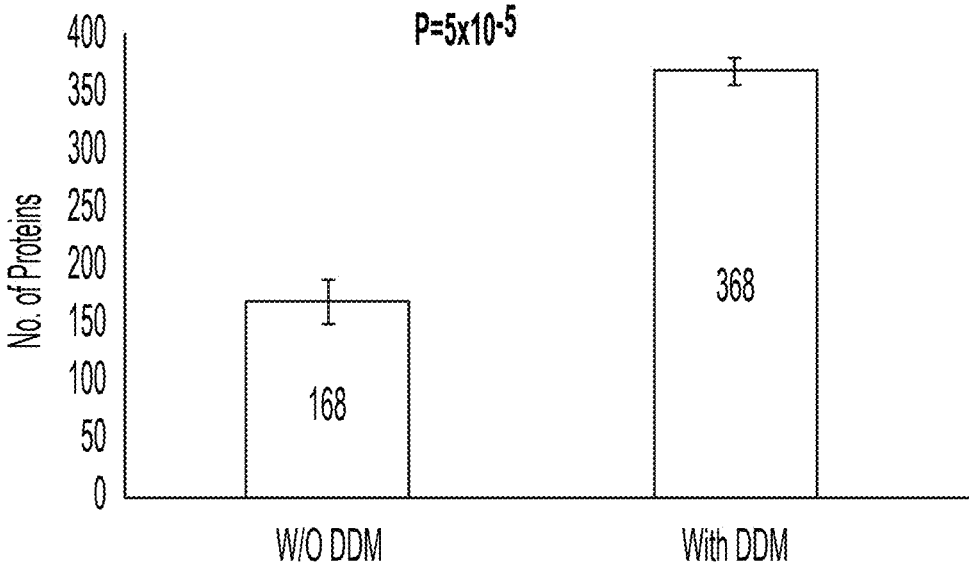
FIG. 1B shows a comparison of protein groups identified using LC-MS/MS with and without DDM using 0.2 ng HeLa cell lysate tryptic digests (single-cell protein amount), according to an exemplary embodiment.

Example 1. Achieving Maximum Hydrophobic Peptide Recovery in Single Cell Proteomics Analysis with DDM To demonstrate the efficacy of DDM in improving or maximizing peptide recovery in single cell proteomics, 0.2 ng HeLa digests were prepared with either DDM or formic acid (FA) solution and analyzed by LC-MS in triplicate. Compared to control samples, the number of identified unique peptides (363 vs 964) and protein groups (168 vs 368) increased significantly in DDM-prepared HeLa digest samples, as shown in FIG. 1A and FIG. 1B. The results indicate that DDM can maximize peptide recovery for single-cell proteomics by greatly reducing peptide loss due to surface adsorption, which also aligns with a previous report (Tsai et al. 2021).

Figure 1C:
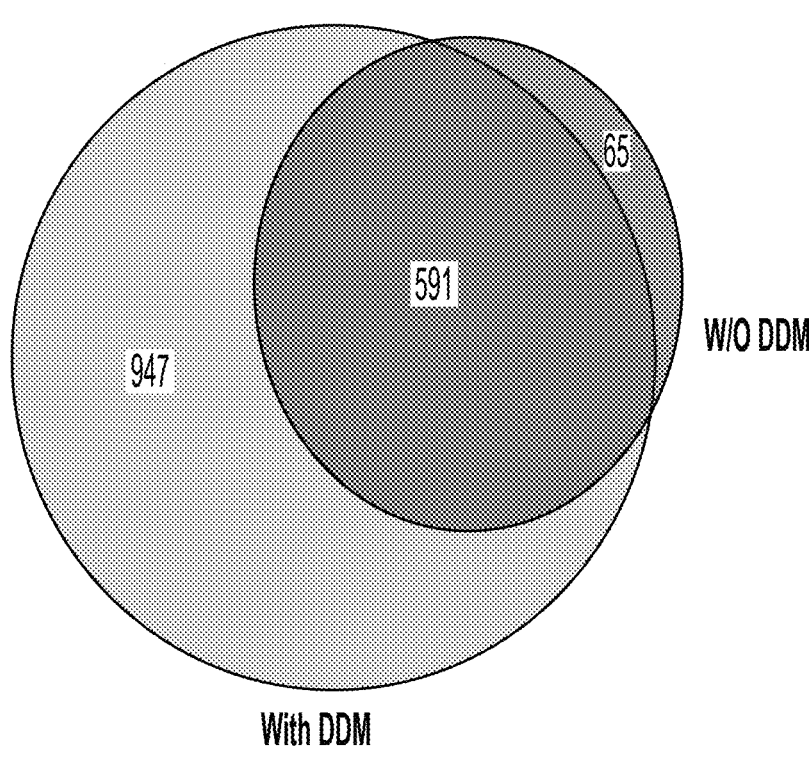
FIG. 1C shows an overlap of total unique peptides identified using LC-MS/MS with and without DDM using 0.2 ng HeLa cell lysate tryptic digests (single-cell protein amount), according to an exemplary embodiment.
Figure 1D:
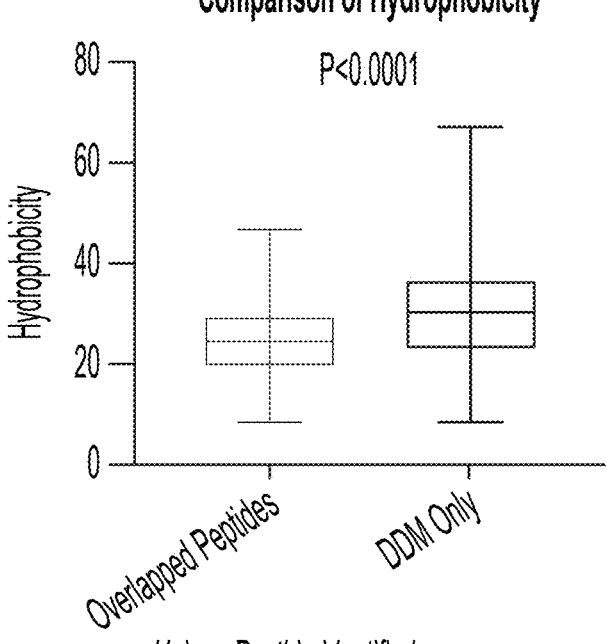
FIG. 1D shows a comparison of peptide hydrophobicity between peptides identified using LC-MS/MS both with and without DDM, compared to peptides identified only with DDM, according to an exemplary embodiment.

Further analysis found that the vast majority of unique peptides (591 of 656) identified in control samples overlapped with the unique peptides identified in DDM-containing samples. Meanwhile, a majority of the total identified unique peptides (947/1603) were identified only in the DDM-containing samples, as shown in FIG. 1C. To better understand the difference between overlapping unique peptides and peptides identified only in DDM samples, peptide hydrophobicity index values were calculated. These results show a significant difference between the two unique peptide groups (p<0.0001) and indicate that peptides identified only in DDM-containing samples were much more hydrophobic than the overlapping peptides, as shown in FIG. 1D.

Figure 2:
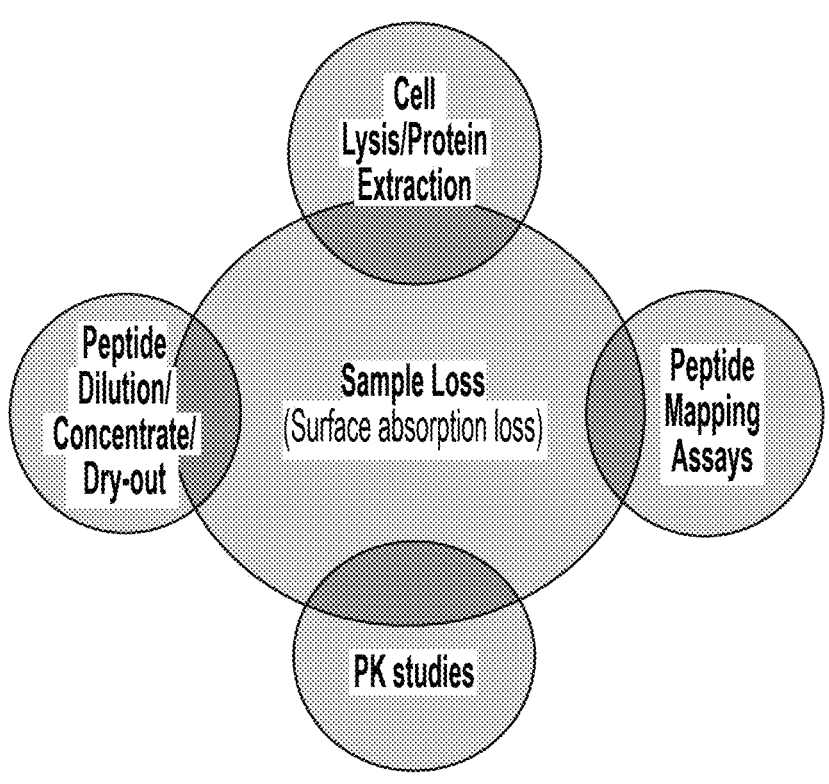
FIG. 2 illustrates applications for which sample loss due to surface adsorption may be an issue, according to an exemplary embodiment.

This analysis suggests that hydrophobic peptide recovery was maximized in the single cell samples by greatly reducing its surface adsorption losses during sample preparation with DDM. However, hydrophobic peptide loss is not unique to single-cell proteomics and is a common issue during protein sample preparation in general, as shown in FIG. 2. These findings indicate that DDM also has the potential to improve various assays during protein drug development in the biopharmaceutical field. Therefore, novel methods were developed using DDM to improve peptide and protein characterization in biopharmaceutical assays.

Figure 3:
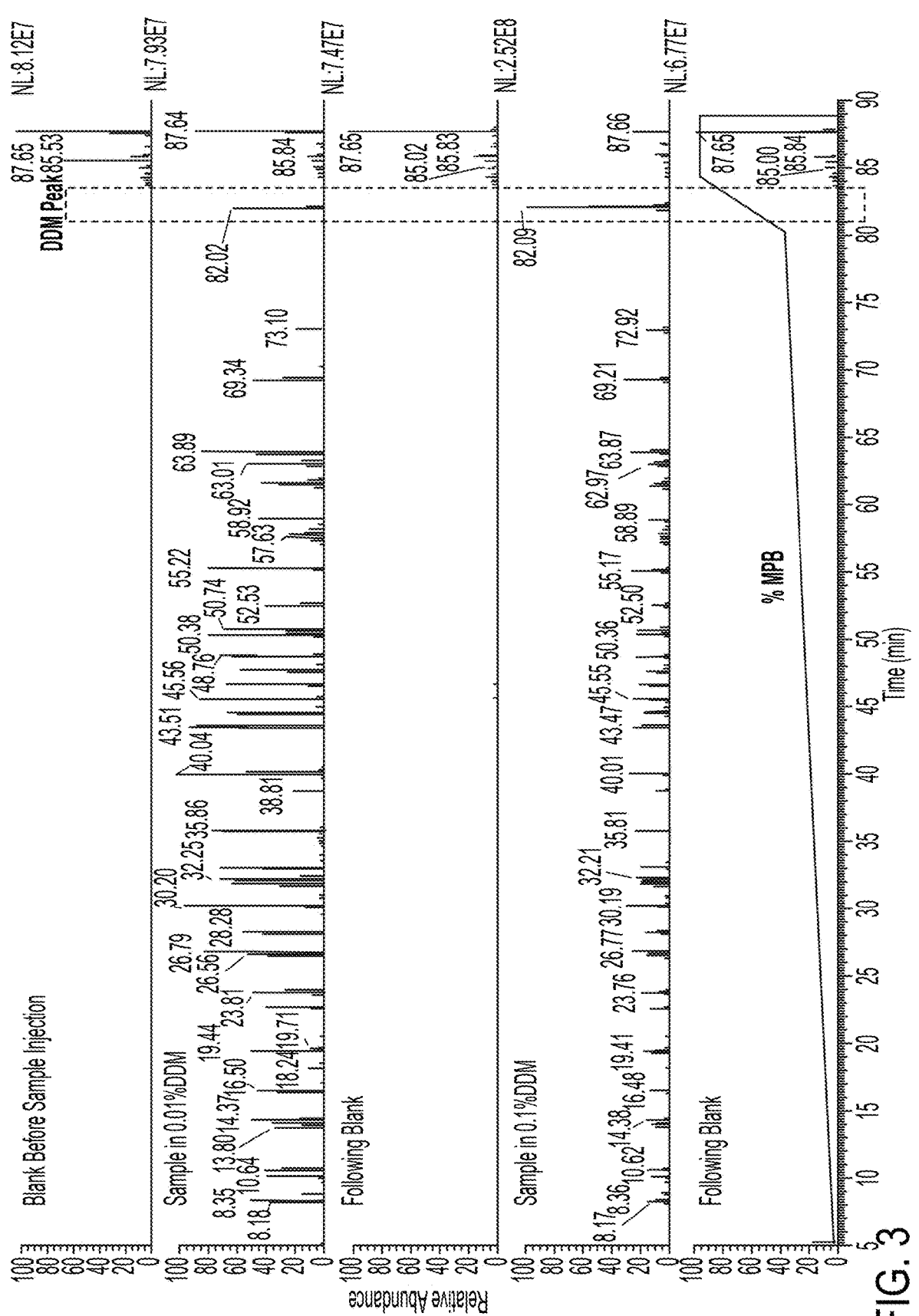
FIG. 3 shows a UPLC-MS analysis demonstrating that DDM eluted after peptide analytes, according to an exemplary embodiment.

Example 2. DDM is a Surfactant Compatible with mAb Drug Characterization Assays It has been previously demonstrated that DDM is a surfactant compatible with nanoLC-MS (Tsai et al. 2021; Liu et al.). Although DDM should not interfere with peptide mapping UV spectra, which are typically monitored simultaneously with UPLC-MS analysis, it is still necessary to test the compatibility of DDM in mAb drug development assays. Peptide mapping characterization of a mAb was executed with different concentrations of DDM (0.01% and 0.1%). The DDM compound eluted after all peptides at about 48% MPB, having no impact on peptide separation or MS detection, as shown in FIG. 3. Additionally, there was no carry-over of DDM in subsequent runs regardless of the DDM concentration used. Finally, highly comparable UV chromatograms were obtained for the DDM-containing samples and controls.

These results demonstrate that DDM is a surfactant compatible with mAb drug development assays, including those requiring simultaneous UV and MS detection or using different solvents than typical nanoLC-MS analyses.

Example 3. Improving Target Peptide Signals in PK Studies by Applying DDM to Synthetic Peptide Standard Preparation In mAb PK studies, CDR peptides must be selected to represent mAb drug proteins in order to monitor concentration changes in patients' serum at different times after drug administration. However, CDR peptides are usually highly hydrophobic, and therefore easy to lose to surface adsorption, especially when dealing with synthetic peptide standards (Perchiacca et al., *Protein Eng Des Sel* 2012, 25, 591-601).

In order to optimize a method for characterizing peptides for PK studies, sixteen peptides from different mAb molecules, including 13 CDR peptides and three constant region peptides, were selected and synthesized. Information for the synthetic peptide standards, including stock concentration, dilution, hydrophobicity index value, and retention time is shown in Table 1. All synthetic peptide standards were diluted and mixed as a single peptide mixture with a final concentration of 10 fmol/$\mu$l using either a DDM solution, formic acid solution (control) or complex HeLa cell lysate digest matrix. PRM acquisition was then used to quantify the peak area of these 16 target peptides and compare results between different samples. Detailed PRM setting information is listed in Table 2 including m/z value and charge states of each target peptide. Each sample was analyzed in triplicate, and average peak areas for each peptide from the DDM prepared samples and matrix prepared samples were compared with the control samples. As shown in Table 1, hydrophobic target peptides showed a significant increase in MS signal in DDM samples, ranging from a two-fold change up to 38-fold change. However, other less hydrophobic peptides and hydrophilic peptides did not show a substantial difference between the DDM samples and control samples. These results indicate that DDM can prevent hydrophobic peptide loss and maximize their recovery when handling synthetic peptide standards used in PK studies.

TABLE 1

Changes in peak area of synthetic mAb peptides for different sample preparation conditions

| | | | | | | Ratio of Average Peak Area | |
|---|---|---|---|---|---|---|---|
| Sequence | Location | Stock Conc. (pmol/$\mu$l) | Fold Dilution | Hydrophobicity Index | Retention Time (Min) | DDM Diluted/FA Diluted | Matrix Diluted/FA Diluted |
| LSCAASGIT FSNAWMS WVR | CDR | 5.0 | 500 | 46.37 | 32.3 | 37.9 | 16.9 |
| LSCAASGF TFSNYAMY WVR | CDR | 5.0 | 500 | 44.95 | 31.6 | 29.4 | 9.2 |
| TNYLKPTH QTNTIIDVV LSPSH | Constant region | 5.0 | 500 | 39.21 | 25.9 | 18.4 | 32.1 |
| VVSVLTVL HQDWLNG K | Constant region | 1000 | 100000 | 39.99 | 35.78 | 12.1 | 33.2 |
| GLEWVAVI SYDGSNK | CDR | 5.0 | 500 | 34.74 | 29 | 10.3 | 4.7 |
| LLIYAASNL ETGVPSR | CDR | 2.0 | 200 | 35.03 | 27.27 | 5.5 | 2.7 |
| DWNQNNW F | CDR | 5.0 | 500 | 29.73 | 31.7 | 2.4 | 3.0 |
| TNYLTHR | CDR | 5.0 | 500 | 11.76 | 16.5 | 1.7 | 0.4 |
| DNSLTAPY VFGTGTK | CDR | 5.0 | 500 | 27.37 | 24.45 | 1.4 | 1.1 |
| DILTGF | CDR | 5.0 | 500 | 25.41 | 30.1 | 1.3 | 1.5 |
| LLIYDASNL K | CDR | 5.0 | 500 | 29.42 | 24.7 | 1.2 | 1.4 |
| DIATYYCQ QH | CDR | 5.0 | 500 | 16.76 | 21.4 | 1.1 | 1.4 |
| VTISCTGSS SNIGTHY | CDR | 5.0 | 500 | 20.63 | 20.6 | 1.1 | 1.4 |
| LMIYDVSK | CDR | 5.0 | 500 | 25.36 | 23.1 | 1.1 | 1.3 |
| DTAVYYCA SGS | CDR | 5.0 | 500 | 24.8 | 14.2 | 0.9 | 0.6 |

TABLE 1-continued

Changes in peak area of synthetic mAb peptides for different sample preparation conditions

| | | | | | | Ratio of Average Peak Area | |
| | | | | | | DDM | Matrix |
| | | Stock | | | | Diluted/FA | Diluted/FA |
| | | Conc. | Fold | Hydrophobicity | Retention | Diluted | Diluted |
| Sequence | Location | (pmol/μl) | Dilution | Index | Time (Min) | | |
|---|---|---|---|---|---|---|---|
| NQVSLTCL VK | Constant region | 1800 | 180000 | 24.97 | 24.79 | 0.7 | 1.1 |

TABLE 2

Synthetic peptide standards used in PRM target quantification

| Sequence | Stable Isotope-Labeled Residue | Internal Modification | m/z | Charge |
|---|---|---|---|---|
| DIATYYCQQH | Isoleucine (I), + 7Da | Cys(CAM) | 653.2857 | 2 |
| DWNQNNWF | Phenylalanine (F), +10 Da | | 567.2468 | 2 |
| DILTGF | Phenylalanine (F), +10 Da | | 675.3777 | 2 |
| VTISCTGSSSNIGTHY | Isoleucine (I), +7 Da | Cys(CAM) | 845.8944 | 2 |
| GLEWVAVISYDGSNK | Lysine (K), +8 Da | | 823.4192 | 2 |
| LMIYDVSK | Lysine (K), +8 Da | | 488.7668 | 2 |
| LSCAASGFTFSNYAMYWVR | Arginine (R), +10 Da | Cys(CAM) | 1121.0102 | 2 |
| LLIYDASNLK | Lysine (K), +8 Da | | 579.3364 | 2 |
| LSCAASGITFSNAWMSWVR | Arginine (R), +10 Da | Cys(CAM) | 1077.5104 | 2 |
| TNYLKPTHQTNTIIDVVLSPSH | | | 1239.653 | 2 |
| TNYLTHR | Arginine (R), +10 Da | | 457.7395 | 2 |
| VVSVLTVLHQDWLNGK | Lysine (K), +8 Da | | 606.0123 | 3 |
| LLIYAASNLETGVPSR | Arginine (R), +10 Da | | 857.4747 | 2 |
| DTAVYYCASGS | Valine (V), +6 Da | Cys(CAM) | 600.2747 | 2 |
| DNSLTAPYVFGTGTK | Lysine (K), +8 Da | | 789.8986 | 2 |
| NQVSLTCLVK | N/A | | 552.8077 | 2 |

Typically, complex tissue/cell sample digest matrix is used to help prevent target peptide loss during peptide standard preparation. These results show that all peptides with significant improvement in DDM-containing samples also have greatly increased MS signal in matrix prepared samples, indicating that both DDM and the matrix solution can prevent hydrophobic peptide loss during peptide standard preparation. However, the complex matrix solution could introduce interference or impact quantitative accuracy, so careful optimization and selection of transitions are necessary for target quantification method development when using the matrix solution. Conversely, there is no interference when DDM is used to handle peptide standard samples.

Figure 4A:
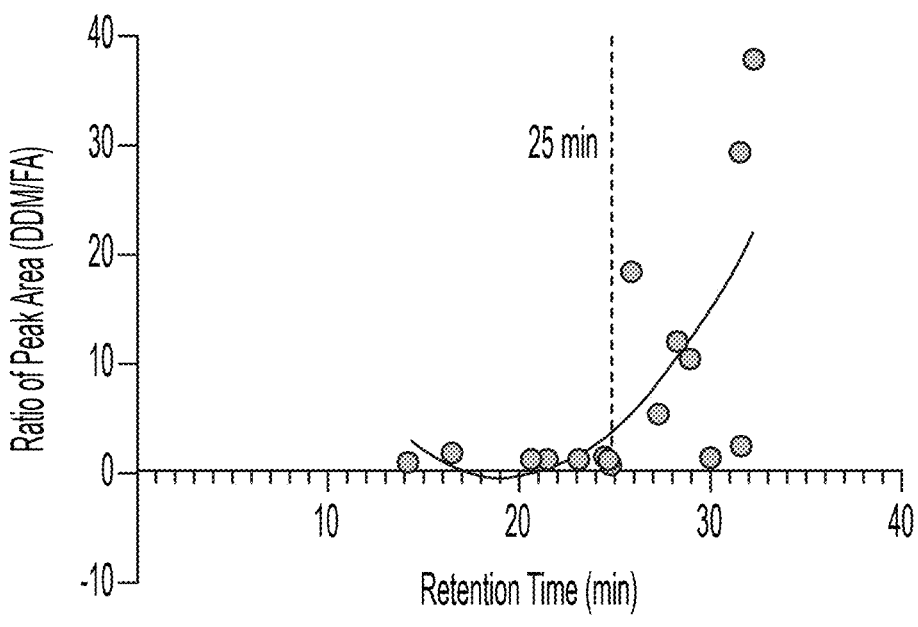
FIG. 4A shows a correlation between peptide retention time and the ratio of peak area between DDM and control samples from synthetic mAb peptide standards, according to an exemplary embodiment.
Figure 4B:
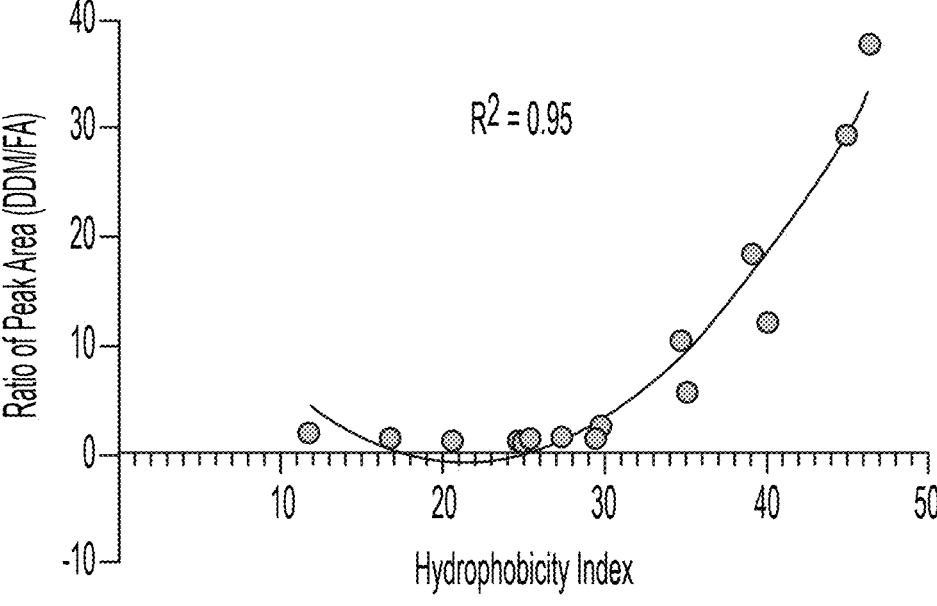
FIG. 4B shows a correlation between peptide hydrophobicity and the ratio of peak area between DDM and control samples from synthetic mAb peptide standards, according to an exemplary embodiment.

Data for the DDM-containing and control samples were further analyzed by comparing the peak area change to the peptide hydrophobicity index value and peptide retention time, as shown in FIG. 4. A strong correlation (R2 value of 0.95) was obtained between peak area change and peptide hydrophobicity, as shown in FIG. 4B. The correlation between peptide peak area ratios and retention time was weaker, but still had a positive correlation (R2 value of 0.46). All later eluting peptides after 25 minutes had a significant increase in their peak area, as shown in FIG. 4A.

These results can provide guidance for target peptide selection and synthetic peptide standard preparation in future PK studies. For hydrophobic peptides or those with a long RT, it is necessary to pay special attention to avoid peptide loss due to surface adsorption.

Example 4. Improving Peptide Mapping Characterization with DDM

Figure 5A:
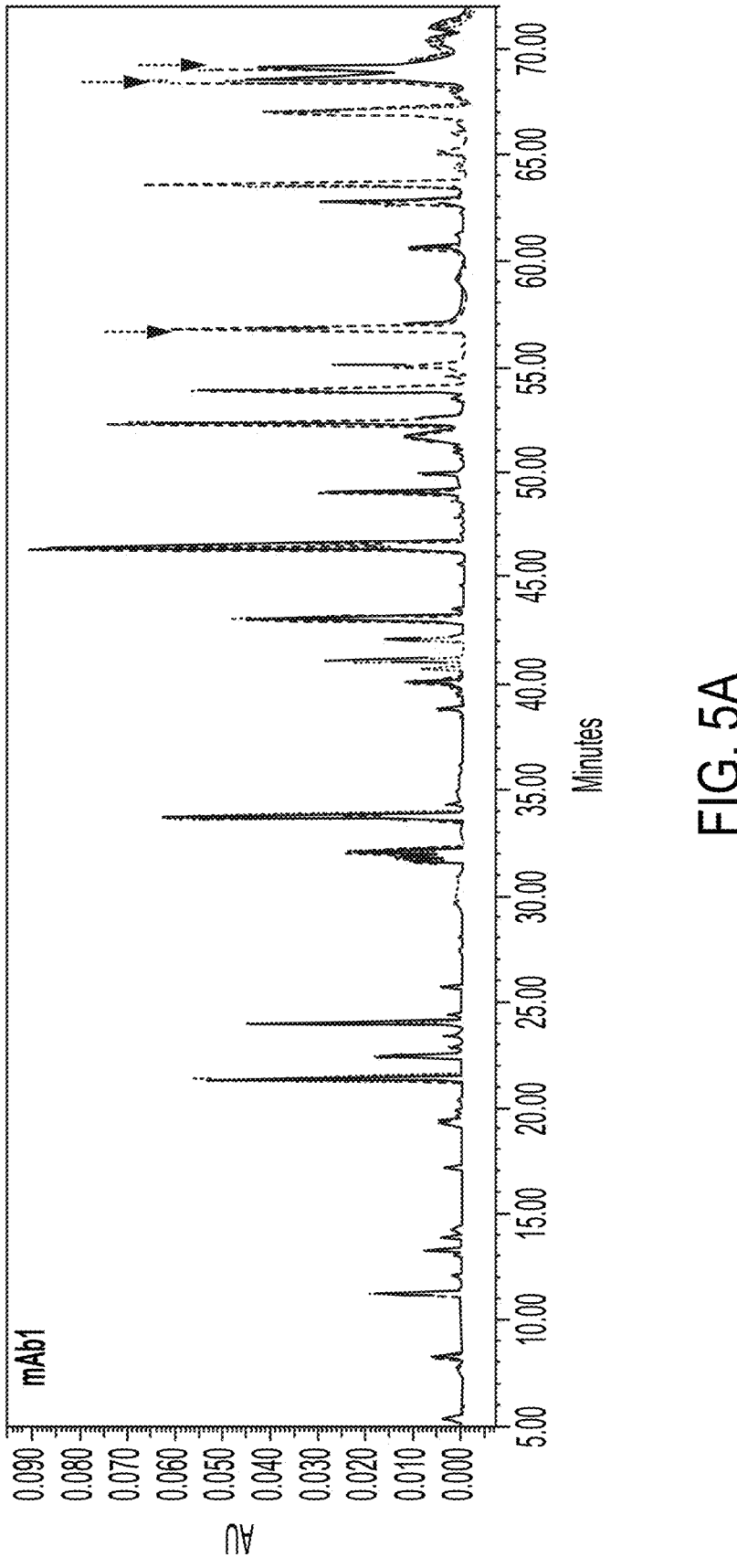
FIG. 5A shows an overlay of UV chromatograms from non-reduced peptide mapping of mAb1 with or without DDM, according to an exemplary embodiment.
Figure 5B:
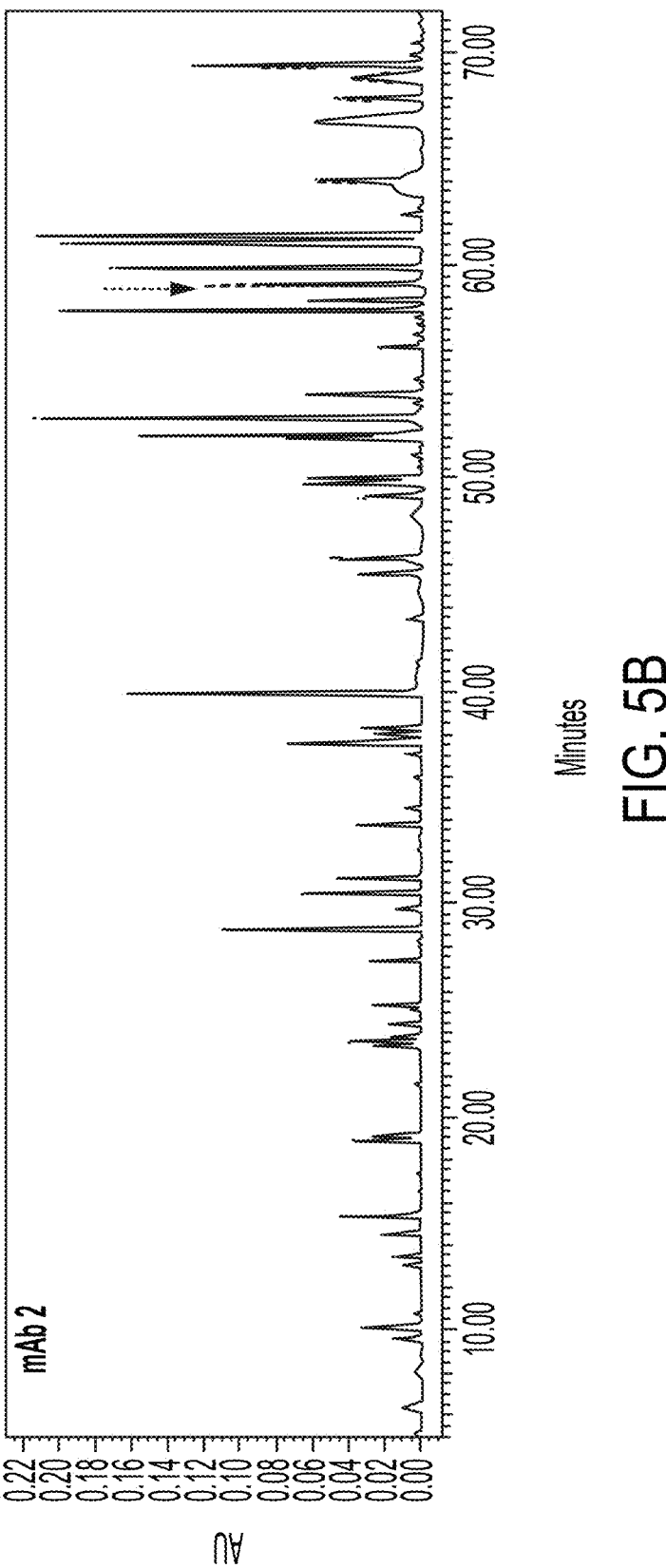
FIG. 5B shows an overlay of UV chromatograms from reduced peptide mapping of mAb2 with or without DDM, according to an exemplary embodiment.

Peptide mapping is a key analytical method for studying the primary structure of biotherapeutic proteins (Bongers et al.; Mouchahoir and Schiel). However, hydrophobic peptide loss often occurs in peptide mapping analyses due to adsorption, which may compromise sequence coverage or result in failure of stability assessments during method qualification (Bongers et al.). Here, a non-reduced peptide mapping (NRPM) experiment and reduced peptide mapping (RPM) experiment were performed on mAb1 and mAb2, respectively. Six individual samples were prepared either with DDM or without DDM for each molecule. Overall, high reproducibility was obtained from the six individual sample preparations in both molecules, as shown in FIG. 5A and FIG. 5B. However, the intensity of three hydrophobic peptides from mAb1 and one hydrophobic peptide from mAb2 were observed to have significant differences between samples with DDM and without DDM, as indicated by the arrows in FIG. 5A and FIG. 5B. These four variable hydrophobic peptides are described in more detail in FIG. 6C. In all four cases, enhanced peptide UV signal in DDM-containing samples was observed.

Two representative peptide peaks, HC128-144 from mAb1 and HC101-120 from mAb2, are shown in FIG. 6A and FIG. 6B, respectively. Peak areas were extracted using Empower and the average from three individual samples were used to calculate the change and RSD. For both peptides, enhanced peptide UV signals were observed in DDM-containing samples. As shown in FIG. 6C, peak intensity of the four hydrophobic peptides increased by about 19% to 64% in DDM-containing samples and their RSDs were reduced significantly from 73% in the control samples to 7% in DDM-containing samples.

Another potential adverse effect of hydrophobic peptide loss on peptide mapping characterization is increased peptide signal variation that could result in failing solution stability test criteria during method qualification. The non-reduced peptide mapping sample from mAb1 was injected on a UPLC-MS for repeated analysis every 12 hours. In total, five runs were analyzed over 48 hours to test peptide solution stability in the autosampler at 4° C. All peptides were found to have great reproducibility except the three hydrophobic peptides discussed above. A gradually decreasing peptide intensity was observed for one peptide (HC128-144) in control samples, but this peptide's intensity was stable in the DDM-containing samples, as shown in FIG. 7A and FIG. 7B. Further analysis found that the RSDs of all three hydrophobic peptides were reduced significantly in the DDM-containing samples compared to the control samples, as shown in FIG. 7C.

These results demonstrate that higher solution stability can be achieved in mAb peptide mapping by adding DDM, which improves the method's robustness and transferability to different sites during drug development and manufacture.

Example 5. Maximizing Peptide Recovery in Dried Sample by Resuspension in DDM Solution Loss of proteolytic peptides following the dry down step by speed-vacuum prior to LC-MS analysis is a common issue in proteomic sample analysis due to the low dissolution of hydrophobic peptides in dried samples using 0.1% TFA or formic acid (Weikart et al.). This example demonstrates the use of a DDM solution to improve hydrophobic peptide recovery from dried samples.

Figure 8:
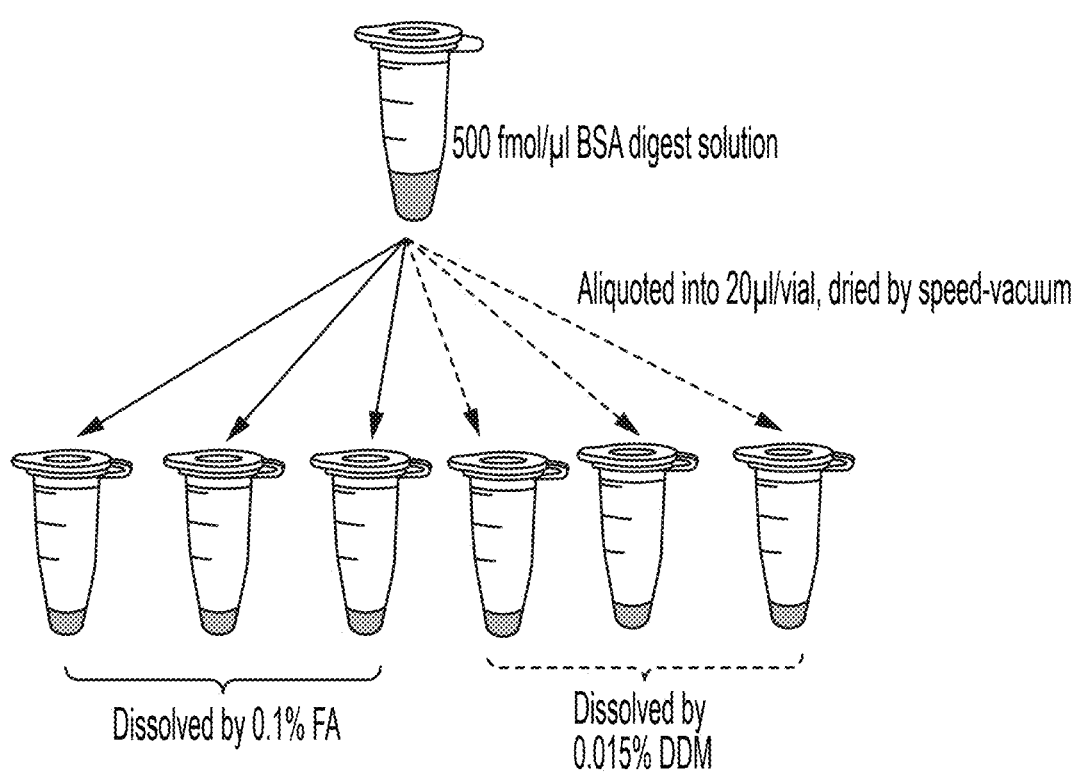
FIG. 8 illustrates an experimental design of an assay for comparing peptide samples reconstituted with FA or DDM, according to an exemplary embodiment.
Figure 9A:
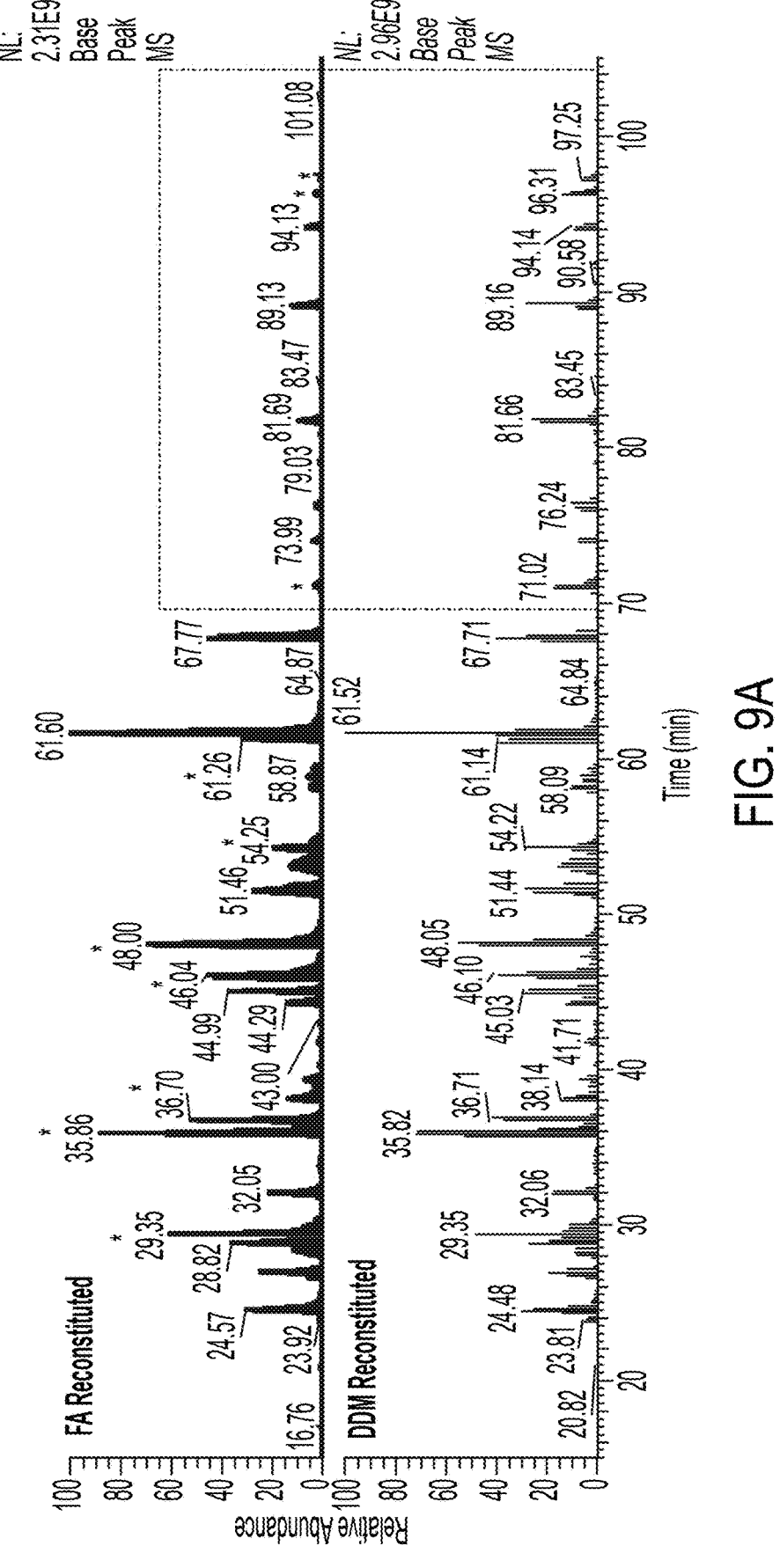
FIG. 9A shows a comparison of peptide peak signals in BSA tryptic peptide samples reconstituted with DDM compared to FA, according to an exemplary embodiment.

Six aliquots of BSA tryptic digests were dried in vacuo and then dissolved by DDM or FA solution, as illustrated in FIG. 8. High coverage of BSA was achieved in both samples, but the peak areas of peptides dissolved in DDM were significantly increased compared to that of 0.1% FA, as shown in FIG. 9A. The difference is especially pronounced for peptides with later retention times, which increase around three-fold in intensity, as indicated by the box in FIG.

Figure 9B:
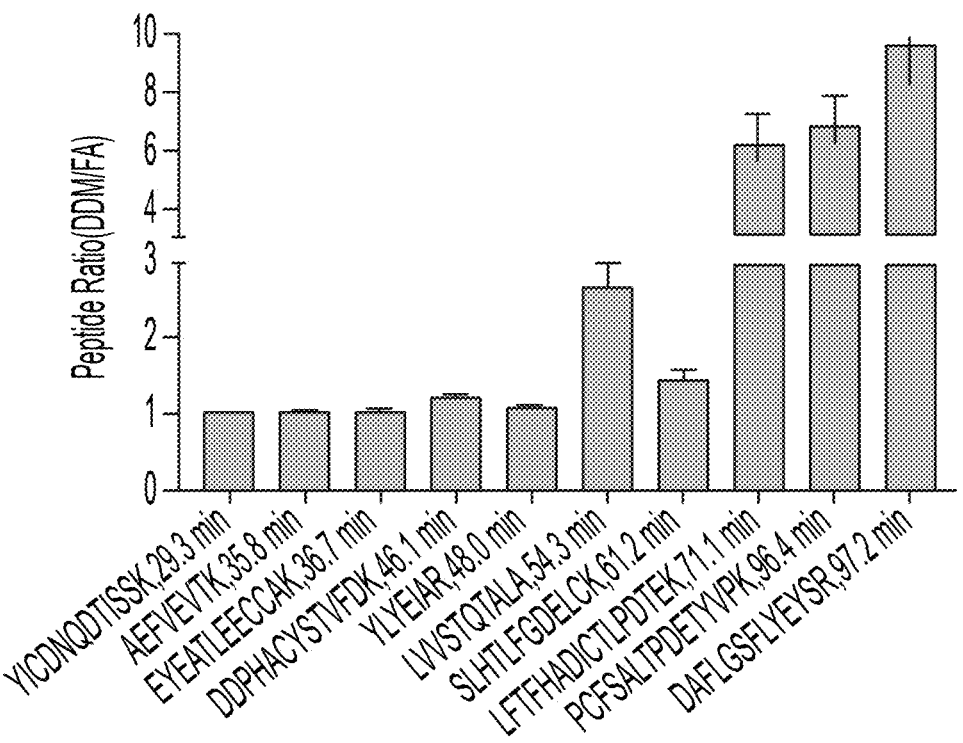
FIG. 9B shows a ratio of peak areas for DDM-dissolved compared to FA-dissolved BSA tryptic peptide samples for ten peptides in order of retention time, according to an exemplary embodiment.

9A. To quantify the peptide peak change, ten landmark peaks from different retention times (indicated by the * in FIG. 9A) were selected and their peak areas were calculated in DDM-dissolved samples and 0.1% FA-dissolved samples, as shown in FIG. 9B. For early eluting peptides, the peak area increased only slightly in DDM-dissolved samples. However, an enhancement of up to ten-fold for later eluting peptides was observed when dissolved using DDM.

Figure 9C:
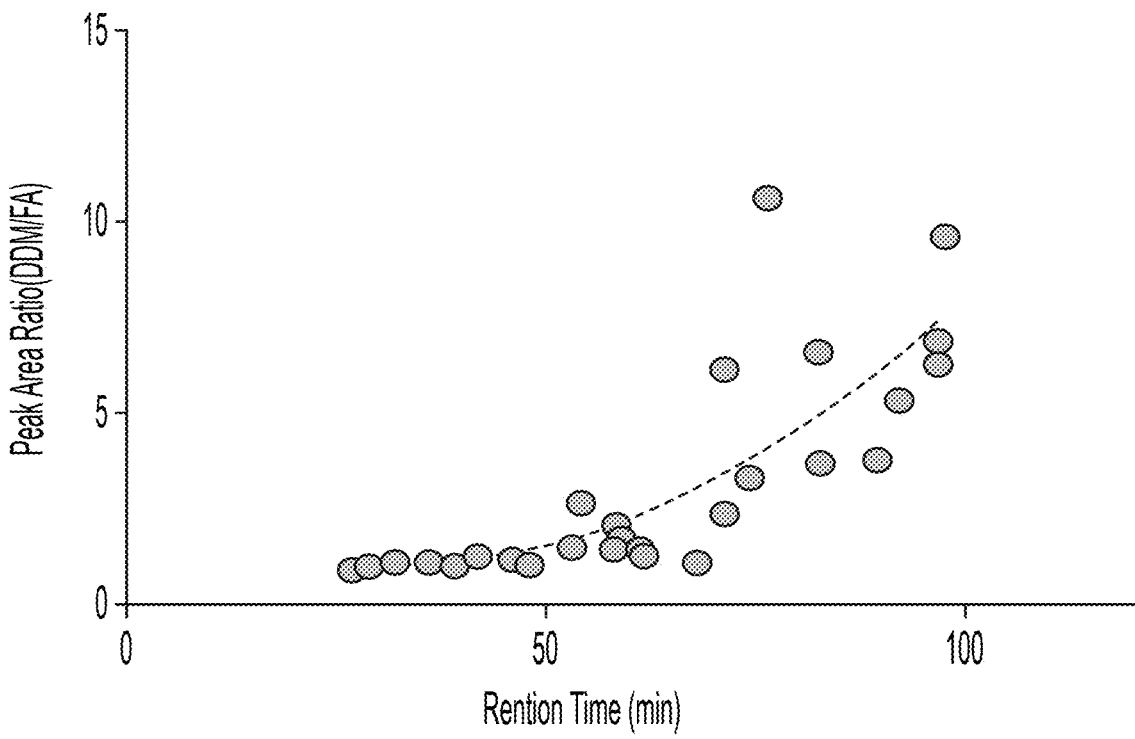
FIG. 9C shows a correlation between peak area ratio for DDM-dissolved compared to FA-dissolved BSA tryptic peptide samples and retention time, according to an exemplary embodiment.

In addition, the retention times of all BSA peptides identified with high confidence were compared with the ratio of peak area change between DDM-dissolved and FA-dissolved samples. As shown in FIG. 9C, a good correlation was obtained between retention time and peak area change ($R^2$ value of 0.68). This is in agreement with the demonstrated effect of DDM on recovering hydrophobic peptides, as the retention time of reversed-phase LC generally correlates with the hydrophobicity of the peptides. These results suggest that dissolution of peptides with DDM considerably improved recovery, especially of the hydrophobic peptides.

Figure 10:
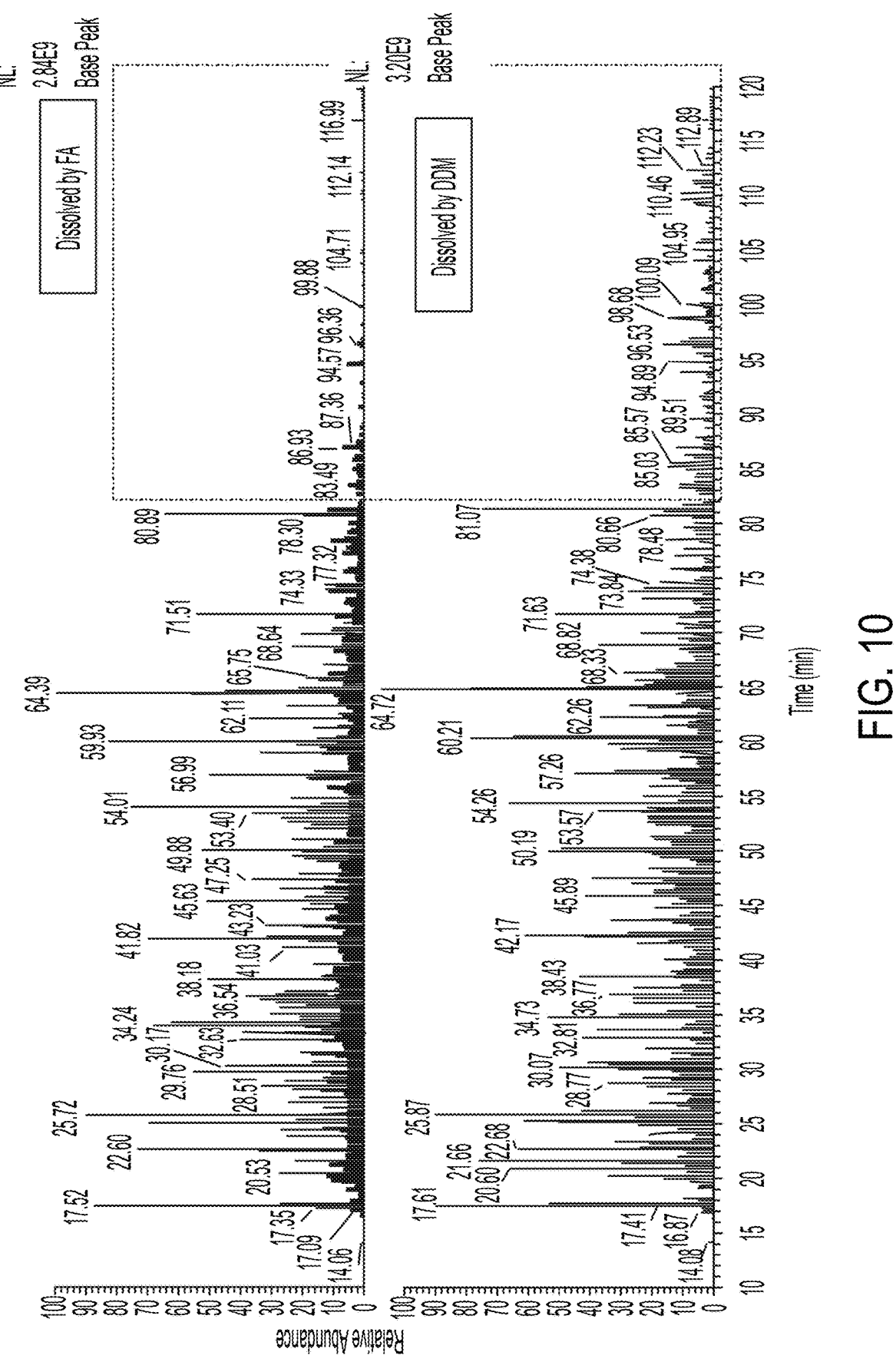
FIG. 10 shows base peak chromatograms of dried HeLa digests dissolved in FA or DDM solutions, according to an exemplary embodiment.
Figure 11A:
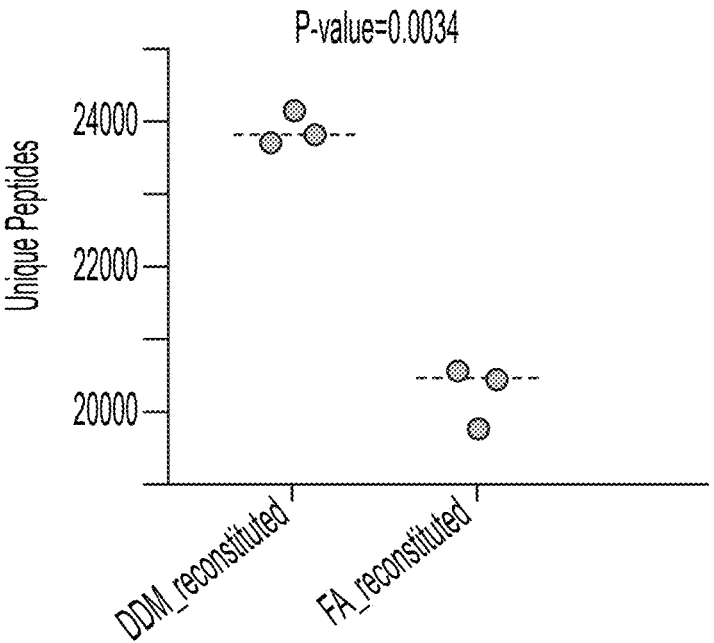
FIG. 11A shows a total number of unique peptides identified from dried HeLa digest samples reconstituted in DDM solution or FA solution, according to an exemplary embodiment.
Figure 11B:
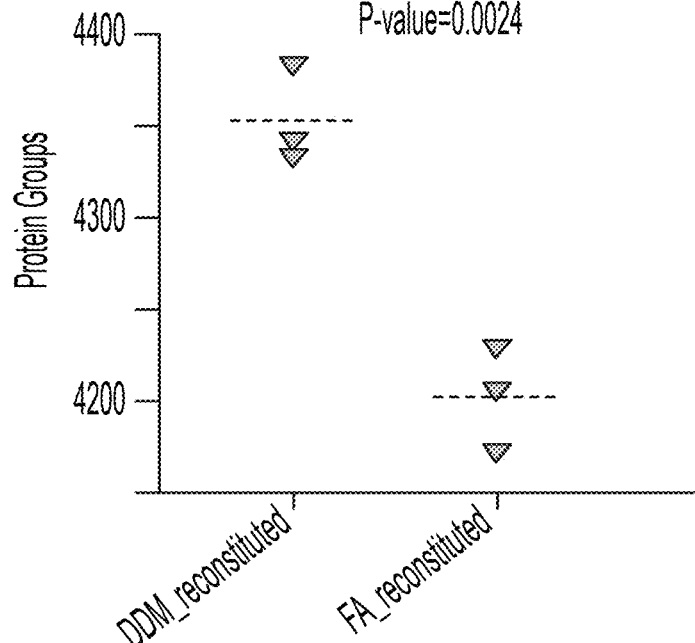
FIG. 11B shows a total number of protein groups identified from dried HeLa digest samples reconstituted in DDM solution or FA solution, according to an exemplary embodiment.

This finding was further demonstrated through the analysis of complex HeLa digest samples dissolved in DDM or FA solution. In the LC-MS chromatograms, significantly enhanced peptide peak signals were observed in later eluting peptide peaks from 82 minutes to 120 minutes, as shown in FIG. 10. Based on a database search, it was found that more than 15% of the unique peptides identified were found only in DDM-dissolved HeLa digest samples as compared to FA-dissolved samples, as shown in FIG. 11A. More proteins were also observed in DDM-dissolved digests than control digests, as shown in FIG. 11B. A T-test analysis was performed to measure the difference in identified peptides and proteins between the samples dissolved in different solvents. Significant p values ($<0.005$) were obtained for both the identified unique peptides and protein groups. These results indicate that dried samples dissolved in DDM-containing solution can enhance the proteome coverage in complex digested samples by maximizing hydrophobic peptide recovery.

The examples described above demonstrate that the non-ionic surfactant, DDM, improves hydrophobic peptide recovery in different samples and sample preparations by preventing hydrophobic peptide surface adsorption loss. Additionally, it has been shown that DDM does not have a negative impact on hydrophilic peptide recovery. These results show that DDM is a surfactant that is completely compatible with different mAb drug development assays without the need for purification steps to remove it.

No impact was observed on peptide separation in UPLC-MS analysis, and no changes were seen in UV absorbance signals in UV/LC-MS analysis when incorporating DDM. In the PK study, significantly improved MS signals were observed for the hydrophobic target peptides. A strong correlation between changes in peptide peak area and peptide retention time or peptide hydrophobicity were found and could provide guidance for target peptide selection and synthetic peptide standard preparation.

In the peptide mapping assay, hydrophobic peptide signal and solution stability were improved with the addition of DDM during sample preparation. This may be helpful to qualify methods and transfer Standard Operating Procedures (SOPs) during protein drug development and manufacturing. In addition, DDM was found to help maximize hydrophobic peptide recovery in dried samples. These findings could help reduce sample loss during complex sample clean-up and enhance proteome coverage in complex sample analysis.

What is claimed is:

1. A method for peptide mapping analysis, comprising:
(a) subjecting a sample including a protein of interest to conditions suitable for denaturing to form a denatured sample;
(b) contacting said denatured sample to at least one alkylating agent under conditions suitable for alkylation to form an alkylated sample;
(c) contacting said alkylated sample to N-dodecyl-β-D-maltoside (DDM) to form a mixture;
(d) contacting said mixture to at least one digestive enzyme under conditions suitable for digestion to form a peptide digest; and
(e) subjecting said peptide digest to liquid chromatography-mass spectrometry for a peptide mapping analysis;
wherein the protein of interest is an antibody having a peptide from a complementarity-determining region (CDR) of the antibody, and wherein the sample with the DDM exhibits an increased signal for the peptide from the CDR relative to a signal for the peptide from the CDR in a sample without DDM.

2. The method of claim 1, wherein said peptide mapping analysis is reduced peptide mapping analysis.

3. The method of claim 1, wherein said protein of interest is a bispecific antibody, a monoclonal antibody, or an antibody-drug conjugate.

4. The method of claim 1, wherein said conditions suitable for denaturing comprise heating said sample, optionally wherein said heating is conducted at about 80° C. for about 10 minutes.

5. The method of claim 1, further comprising subjecting said sample to conditions suitable for reduction.

6. The method of claim 5, wherein said conditions suitable for reduction comprise contacting said sample to Tris (2-carboxyethyl) phosphine hydrochloride (TCEP-HCl), optionally wherein a concentration of said TCEP-HCl is about 5 mM.

7. The method of claim 1, wherein said at least one alkylating agent comprises iodoacetamide.

8. The method of claim 1, wherein a final concentration of DDM in said mixture is about 0.1%.

9. The method of claim 1, wherein said at least one digestive enzyme comprises trypsin, optionally wherein said trypsin is present at an enzyme to substrate ratio of about 1:10 (w/w).

10. The method of claim 1, wherein said liquid chromatography-mass spectrometry comprises reversed-phase liquid chromatography, ion exchange chromatography, size exclusion chromatography, affinity chromatography, hydrophobic interaction chromatography, hydrophilic interaction chromatography, mixed-mode chromatography, or a combination thereof.

11. The method of claim 1, wherein said liquid chromatography-mass spectrometry comprises a mass spectrometer coupled to liquid chromatography, and said mass spectrometer is an electrospray ionization mass spectrometer, nano-electrospray ionization mass spectrometer, or an Orbitrap-based mass spectrometer.

12. The method of claim 1, wherein said liquid chromatography-mass spectrometry analysis comprises parallel reaction monitoring analysis.

13. The method of claim 1, wherein the peptide mapping analysis further comprises obtaining an ultraviolet signal of the peptide from the CDR by an ultraviolet spectrometer coupled to the liquid chromatography-mass spectrometry.

14. The method of claim 13, wherein the sample with the DDM exhibits an increased ultraviolet signal for the peptide from the CDR relative to an ultraviolet signal for the peptide from the CDR in a sample without DDM.

15. The method of claim 13, wherein the sample with the DDM exhibits the ultraviolet signal with a reduced relative standard deviation (RSD) for the peptide from the CDR relative to a ultraviolet signal of the peptide from the CDR in a sample without DDM.

16. The method of claim 1, wherein the peptide digest is dried and reconstituted with a solution including N-dodecyl-β-D-maltoside prior to subjecting said peptide digest to the liquid chromatography-mass spectrometry for the peptide mapping analysis.

17. The method of claim 1, wherein a final concentration of DDM in said mixture is from about 0.01% to about 0.1%.

18. The method of claim 1, wherein said peptide mapping analysis is a non-reduced peptide mapping analysis.

* * * * *